(12) United States Patent
Peterson

(10) Patent No.: US 7,392,559 B2
(45) Date of Patent: Jul. 1, 2008

(54) METHOD AND APPARATUS FOR MANUFACTURING CUSTOM ORTHOTIC FOOTBEDS

(75) Inventor: William E. Peterson, Newport, RI (US)

(73) Assignee: Esoles L.L.C., Scottsdale, AZ (US)

( * ) Notice: Subject to any disclaimer, the term of this patent is extended or adjusted under 35 U.S.C. 154(b) by 351 days.

(21) Appl. No.: 11/116,738

(22) Filed: Apr. 28, 2005

(65) Prior Publication Data

US 2006/0283243 A1    Dec. 21, 2006

(51) Int. Cl.
  *A43D 1/00*    (2006.01)
(52) U.S. Cl. .................. 12/1 R; 12/142 R; 33/3 R; 33/6
(58) Field of Classification Search .............. 12/1 R, 12/142 R, 142 N; 33/3 R, 6, 3 B, 3 C
See application file for complete search history.

(56) References Cited

U.S. PATENT DOCUMENTS

| | | | | |
|---|---|---|---|---|
| 4,454,618 A | * | 6/1984 | Curchod | 12/1 R |
| 4,510,636 A | * | 4/1985 | Phillips | 12/1 R |
| 4,745,290 A | | 5/1988 | Frankel et al. | |
| 5,054,148 A | | 10/1991 | Grumbine | |
| 5,237,520 A | * | 8/1993 | White | 382/154 |
| 5,282,328 A | | 2/1994 | Peterson | |
| 5,339,252 A | | 8/1994 | White et al. | |
| 5,477,371 A | | 12/1995 | Shafir | |
| 5,659,395 A | | 8/1997 | Brown et al. | |
| 5,671,055 A | | 9/1997 | Whittlesey et al. | |
| 5,689,446 A | | 11/1997 | Sundman et al. | |
| 5,689,849 A | * | 11/1997 | Charles | 12/146 M |
| 5,790,256 A | | 8/1998 | Brown et al. | |
| 6,006,412 A | * | 12/1999 | Bergmann et al. | 29/407.04 |
| 6,042,759 A | | 3/2000 | Marshall | |
| 6,141,889 A | | 11/2000 | Baum | |
| 6,523,206 B2 | | 2/2003 | Royall | |
| 6,654,705 B1 | | 11/2003 | Benson et al. | |
| 6,692,454 B1 | | 2/2004 | Townsend et al. | |

(Continued)

FOREIGN PATENT DOCUMENTS

EP    0829209 A1    3/1998

(Continued)

OTHER PUBLICATIONS

International Search Report for PCT/US2006/016,116, dated Sep. 28, 2006.

(Continued)

*Primary Examiner*—Marie Patterson
(74) *Attorney, Agent, or Firm*—George A. Herbster

(57) ABSTRACT

A method and apparatus for providing a topographical map of the bottom of a patient's rear foot with the foot in a semi-weight bearing condition and in the neutral position. A flexible membrane defines the top of an air cushion that captures the patient's foot in the neutral position when the air pillow is inflated. The membrane also conforms to the bottom of the foot. A three-dimensional scanner located below the membrane measures the distances to the bottom of the membrane over an array of positions. A manufacturing facility converts these measurements into information by which computer numerical controlled equipment machines an orthotic insert for the patient's footwear.

30 Claims, 21 Drawing Sheets
(3 of 21 Drawing Sheet(s) Filed in Color)

U.S. PATENT DOCUMENTS

| | | | |
|---|---|---|---|
| 2001/0002232 A1 | 5/2001 | Young et al. |
| 2004/0168329 A1 | 9/2004 | Ishimaru |
| 2006/0103852 A1 | 5/2006 | Klaveness |

FOREIGN PATENT DOCUMENTS

| | | |
|---|---|---|
| EP | 00990398 A2 | 5/2000 |
| GB | 434733 | 9/1935 |
| JP | 2004219404 | 8/2004 |
| WO | 98/18386 | 5/1998 |
| WO | WO 02/34157 A2 | 5/2002 |
| WO | WO03/087717 | 10/2003 |

OTHER PUBLICATIONS

Written Opinion of the International Searching Authority for PCT/US2006/016,116, dated Sep. 28, 2006.

* cited by examiner

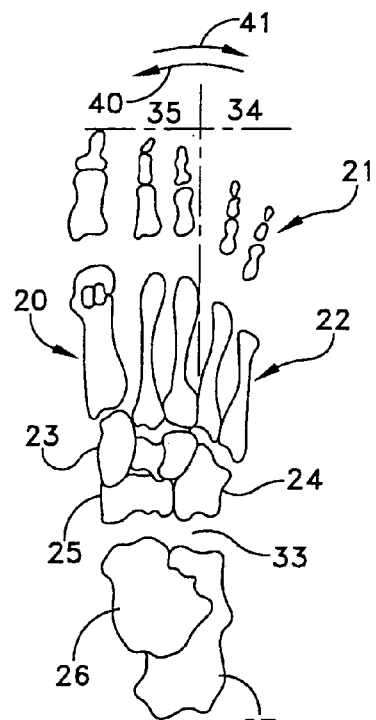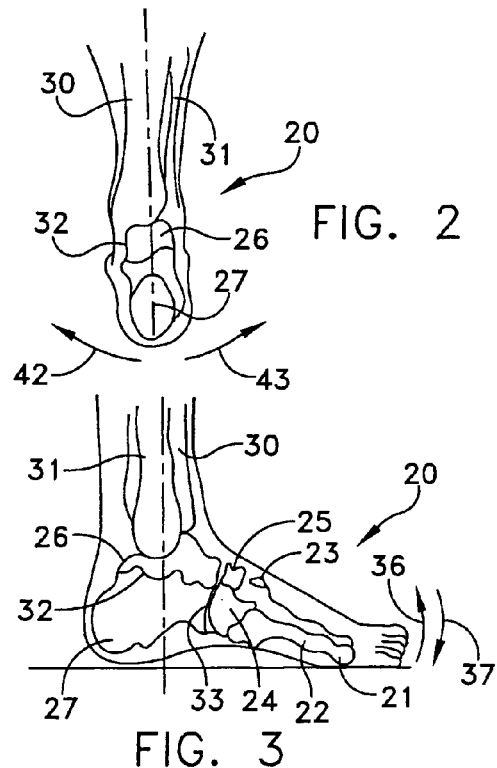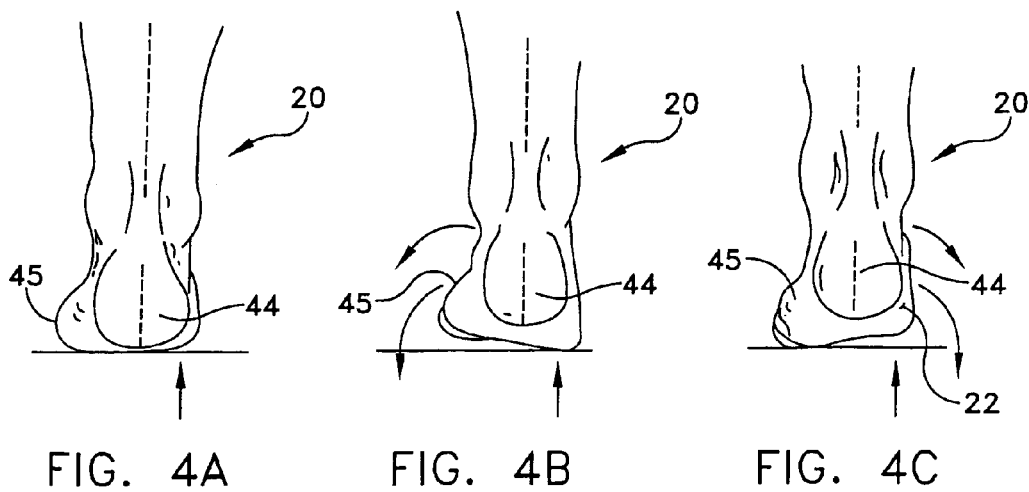

EVALUATION

Family Name_____ First Name_____ Referal_____

Date___/___/___ Address_____ City_____ State_____ Zip_____

Age_____ DOB___/___/___ Weight_____ Phone (Hm)_____ (Wk)_____

Occupation_____ Activities:_____

Arthritis___Where_____ Diabetic___HowLong_____ Users:

Complaints: Forefoot/Arch/Heel (spur/burst) / Achilles Tendon/Ankle/Shin/Knee) / Hip/Back/Sciatic Complaint: #1       #2
Surgeries:
(Dates)

| | |
|---|---|
| Anatomical Arch Height R_____mm L_____mm | Forefoot R Neu / Varus / Valgus_____mm |
| Compensated Arch R_____mm L_____mm | L Neu / Varus / Valgus_____mm |
| Pseudoequines Heel-FF _____ | Leg Length Discrepancy (Short Side)_____ (Functional / Measured) |
| TRANSVERSE PLANE | |
| Measured Alignment R_____Int/Ext L_____Int/Ext   Walk/Run Alignment R_____Int/Ext L_____Int/Ext | |
| Bunion R / L   Hallux Valgus R_____ — L_____ — Neuroma R_____ L_____ | |

A                          V

SHOE Type_____ Size_____    SHOE Type_____ Size_____

Orthotic Type_____ Arch_____ Cover_____ FF Post_____ HEEL___ Date Out

Orthotic Type_____ Arch_____ Cover_____ FF Post_____ HEEL___ Date Out

Orthotic Type_____ Arch_____ Cover_____ FF Post_____ HEEL___ Date Out

Met Bar/Pad_____ Lifts: Heel_____ FF_____ Footware Modification:

Follow-up:

FIG. 17

METHOD AND APPARATUS FOR MANUFACTURING CUSTOM ORTHOTIC FOOTBEDS

FIELD OF THE INVENTION

This invention generally relates to foot orthotics and more specifically to a methodology and apparatus for producing custom orthotic footbeds acceptable for therapeutic applications as defined by medical personnel.

DESCRIPTION OF RELATED ART

An individual should stand with each of his or her feet in an optimal anatomical position called a "referenced neutral position." However, in most individuals the foot naturally assumes a position that is different from that referenced neutral position. Orthotic footbeds are inserted into footwear, such as a shoe, to reposition the foot to that referenced neutral position or as close to that position as the individual can tolerate.

Many methods exist for producing orthotic footbeds that support a foot in the referenced neutral position. The gold standard and dominant methodology used by medical personnel for producing orthotic footbeds involves forming a cast and mold. In accordance with this process, a practitioner, who may be a doctor, podiatrist, or other highly trained health care professional, manually manipulates the patient's foot in a non-weight bearing condition into the referenced neutral position. A non-weight bearing condition exists when no forces are applied to the foot, as when the foot is suspended in air. The practitioner further manipulates the foot to compensate for any observed anatomical deformities of the foot.

Once this position has been attained, the practitioner places wet plaster on the bottom of one foot. The practitioner then must holds this foot in this position manually until the plaster dries to form a cast. Then the practitioner repeats the process for the other foot, if two orthotics are to be made. Each cast is a negative impression of the bottom of one of the patient's feet in a non-weight-bearing condition. This process is open to a variety of uncontrolled influences or variables, so casts are not consistent from practitioner to practitioner. Even casts made by the same practitioner may also not be consistent. Further, the requirements attendant with mixing wet plaster, applying it and cleaning equipment and an area after the casts are made presents the practitioner with practical environmental issues.

A practitioner requires a significant time to make such a cast and ship it to a laboratory. Often a practitioner speeds 30 minutes or more to examine a patient, to produce and ship the casts and to clean after the casts are made. This limits the number of patient appointments a single practitioner can keep in a day.

There are two basic business models for the process of transforming patient casts into orthotic footbeds. In as first, a practitioner is collocated with a laboratory. In accordance with the second, more common, model, a central laboratory serves multiple practitioners at different locations. In whichever model, laboratory personnel receive the cast and information about the patient. As an initial step, personnel at the laboratory use the cast to form a positive mold that replicates the bottom of the patient's foot in the non-weight-bearing condition. The production of the mold destroys the original plaster cast is destroyed.

Laboratory personnel use the patient information, a priori knowledge of the practitioner's procedures and other experience to modify the patient's molds. For example, personnel at the laboratory may modify the molds to account for inconsistencies between different casts and to compensate for two significant differences that appear when a foot moves between non-weight-bearing and weight-bearing conditions. The full weight-bearing condition exists when the patient stands with his or her weight distributed evenly on both feet. Specifically as a foot moves from a non-weight-bearing condition to a full weight-bearing condition, the arch lowers or flattens and the foot tends to elongate. As the cast is formed with a non-weight-bearing condition, laboratory personnel may elongate the mold and reduce its arch height based upon patient information, such as patient weight, shoe size, arch height and flatness measurements and a priori knowledge. Laboratory personnel may also modify the mold to take any anatomical deformation into account. However, these modifications generally are based upon averages and experience; they are also time consuming. Moreover, if the orthotic only support the rear foot, any correction for anatomical deformation can be ineffective.

Next personnel at the laboratory use each mold to form a corresponding orthotic block which is finished at the laboratory and returned to the practitioner as an orthotic footbed. The practitioner then dispenses the orthotic footbed to the patient. If a patient reports only little or no relief, the practitioner must reevaluate the patient. If changes to the orthotic footbed are required, then either the entire process must be repeated or the orthotic footbed must be sent back to the laboratory with instructions for additional corrections.

As will be apparent, this methodology is labor intensive. As described, the process involves considerable time of the practitioner. Times from 60 to 90 minutes to complete orthotics at the laboratory are typical. The methodology at the laboratory, like that at the practitioner's location, introduces environmental issues particularly in the handling of the casts and mold manufacture modification. Consequently, there have been significant efforts expended to evolve alternative processes that provide orthotic footbeds that are equal to or greater in quality than those produced by the molding process in order to eliminate much of the complexity and time involved in that process.

For example, my U.S. Pat. No. 5,282,328 discloses a pillow set of left and right foot composite foam pillows for positioning feet toward the referenced neutral foot position. These pillow sets do facilitate the production of custom footbeds. However, each pillow set based upon averages for people in a design weight range. Consequently although the footbed is adequate and provides improvements for many applications, these pillows can introduce minor errors or deviations from the optimum for that individual. Footbeds are produced on these pillows with the feet in either a full weight-bearing condition or a semi-weight-bearing condition. A semi-weight-bearing condition exists when a patient sits so only the weight of the leg produces forces on the bottom of the foot. Footbeds made with the feet in a full weight-bearing condition are particularly adapted for insertion in ski boots or other footwear when the individual's feet will be subjected to various dynamic forces. However, it can be difficult to achieve complete anatomical alignment when these composite foam blocks are used in the full weight-bearing condition. When the composite foam blocks are used in a semi-weight bearing mode, it is easier to achieve such an anatomical alignment and to compensate for certain deformities. However, it can be challenging to position the feet properly to achieve this result, so the process tends to be time consuming.

U.S. Pat. No. 6,141,889 to Baum discloses a custom foot support and method for producing such a foot support based upon a scan of the foot. According to the disclosure, an optical scanner captures a three-dimensional image of the bottom of the foot in a non-weight bearing, semi-weight bearing or full weight bearing condition. The captured images from this scanner are then exported to a central system for use in the production of a footbed. Data relating to patient sex, weight, age, foot type and shoe style serve to modify the captured images. Some of this data is taken from tables based upon averages. So it is unlikely that a modification based upon an average will produce the exact modification the patient requires. The data producing the modified images serves as an input to a CNC machine for forming both the top and bottom surfaces of the foot support. Consequently such foot supports may achieve only some of the objectives that would be achieved by the gold standard approach.

U.S. Pat. No. 6,654,705 to Benson et al. is an example of a system for detecting a surface contour of the human foot with an array of biased, vertically displaceable sensing pins. In these systems an individual stands on a support plate. The pins extend through the plate until they contact the bottom of the foot to provide an array of measurements. In the Benson et al. patent, a person places a foot on an upper support plate that deflects downwardly until the pins pass through the plate and contact a portion of the foot. As each pin contacts the foot, further downward displacement displaces the pin. A counter records decrements of vertical movement for each pin. A final count, when the system is in equilibrium, corresponds to the relative vertical displacement of a corresponding foot position in relation to a reference plane. In other embodiments, the pins are driven upward through the support plate pneumatically until they contact the bottom of the foot. Then the system is "locked" to obtain measurements of the deflection of each pin. In both systems the final information for all the pins provides a digital representation of the sensed contour of the foot. This digital data provides a contour image of the foot and medical information concerning the shape of the foot. As the measurements are made in the full weight-bearing condition, the foot tends to be elongated and the arch tends to flatten. Further, the spatial resolution of the measurements does not provide an accurate representation of the bottom of the foot for medically acceptable orthotics.

U.S. Patent Application Publication No. 2001/0002232 to Young et al. discloses a method and system for forming custom shoe insoles or footbeds by positioning a foot at a scanning station. The scanning station includes at least one laser unit which scans an undersurface of the foot in a full weight-bearing condition on a flat transparent plate. The measured surface coordinates are processed and transmitted to a computer. A milling station, in communication with the scanning station and computer, includes a milling assembly for forming the custom-made insole. As the foot is scanned in the full weight-bearing condition, the arch is flattened and the foot is elongated. Moreover, there is no guarantee that the resulting insoles will support the patient's feet in the referenced neutral positions and accommodate any anatomical deformation.

Each of the foregoing and other alternatives for providing measurements without the use of casts and molds can reduce the labor involved and provide the information without the need for the problems of producing casts and the like. However, practitioners who prescribe orthotic footbeds, particularly for medical reasons, continue to use the gold standard by making plaster casts and molds despite the disadvantages of the labor intensity process and complexity. What is needed is an apparatus and method for producing medically acceptable orthotic footbeds that have the quality of the prior art gold standard but that account for arch lowering and elongation not achieved when measurements are made in a non-weight-bearing condition. What is also needed is a method and apparatus that facilitates the measurement of the bottom of the foot in a referenced neutral position thereby to provide information for the automated manufacture of orthotics that correct for various problems a patient may have with his or her feet. In addition, what is needed is a method and apparatus that produces a medically acceptable orthotic footbed without the attendant labor and environmental issues.

SUMMARY

Therefore it is an object of this invention to provide a method and apparatus for facilitating the generation of information useful in producing medically acceptable orthotic footbeds for insertion in an individual's footwear.

Another object of this invention is to provide a method and apparatus for facilitating the generation of information about the contour of an individual's foot in a referenced neutral position.

Still another object of this invention is to provide medically acceptable orthotic footbeds that supports an individual's foot in footwear in the referenced neutral position and while accommodating certain anatomical foot deformities.

Yet another object of this invention is to provide a method and apparatus for generating information about the contour of a foot that minimizes the use of a priori knowledge in the production of orthotic footbeds.

Still yet another object of this invention is to provide a method and apparatus for facilitating the generation of information about the contour of the foot at multiple locations that facilitates the transfer of those measurements to a central manufacturing facility.

Yet still another object of this invention is to enable the production of a medically acceptable orthotic footbed while eliminating the need for the practitioner to produce a cast and for laboratory personnel to make a mold.

In accordance with one aspect of this invention, measurements that serve as a basis for the construction of an orthotic block for use in orthotic footbeds are obtained by defining a reference plane and capturing the foot in a semi-weight bearing, referenced neutral position with the forefoot supported on the reference plane and with the rear foot floating. An array of measurements is obtained wherein each measurement represents the distance between the reference plane and a corresponding array position on the bottom of a portion of at least the rear foot. These measurements are stored to serve as an input to automated manufacturing equipment that produces an orthotic block.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a transverse view of an individual's right foot;

FIG. 2 is a view of the foot of FIG. 1 in the frontal plane, but viewed from the rear;

FIG. 3 is a view of the foot of FIG. 1 in a sagittal plane viewed from the right;

FIGS. 4A, 4B and 4C depict a rear view of the foot for purposes of explaining varus and valgus anatomical deformities;

FIG. 17 is an example of an evaluation form that can be used in the process of FIG. 16;

DESCRIPTION OF ILLUSTRATIVE EMBODIMENTS

Figure 5A:
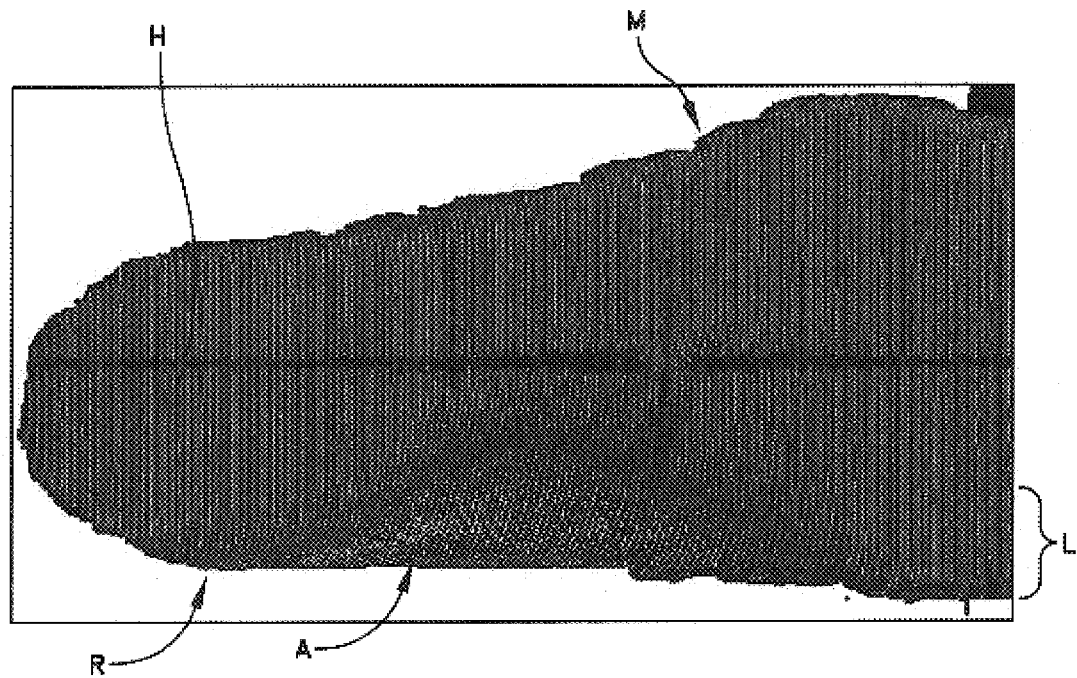
FIGS. 5A and 5B depict scans obtained of a right foot in the semi-weight-bearing and full weight-bearing conditions, respectively, on a flat surface as used in the prior art.

Before discussing a specific embodiment of this invention, it will be helpful to discuss the anatomy of a foot as show in FIGS. 1 through 3 and 4A through 4C that depict the various bones and joints in a right foot and lower leg 20 and conditions that are important to this invention. Referring to FIG. 1 the phalanges 21 form the toes. They are collectively the "forefoot" in this disclosure, and they connect to the midfoot that includes metatarsals 22, cuneiforms 23, the cuboid 24 and navicular 25. The rear foot includes talus 26 and the calcaneus 27. The calcaneus 27 interconnects the foot to the tibia 30 and the fibula 31. A subtalar joint 32 constitutes the interface between the talus 26 and the calcaneus 27. A midtarsal joint 33 comprises the interface between the cuboid 24, navicular 25, talus 26 and the calcaneus 27.

The foot is divided into two columns. As shown in FIG. 1 a lateral or lateral load-bearing column 34 comprises the calcaneus 27, the cuboid 24 and the fourth and fifth ray of the phalanges 21 and metatarsals 22. This represents the outer portion of the foot including the fourth and fifth toes. A medial or medial dynamic column 35 comprises the talus 26, the navicular 25, the cuneiforms 23 and rays one, two and three of the metatarsals 22 and phalanges 21. This corresponds to the inner section of the foot including the first three toes or digits.

Component motions in single planes often define complex motions and include dorsiflexion and plantar flexion in the sagittal plane, adduction and abduction in the transverse plane, and inversion and eversion in the frontal plane. As shown in FIG. 3 the foot undergoes dorsiflexion when the distal end of the foot elevates toward the leg as represented by arrow 36; plantar flexion is the reverse motion as represented by arrow 37. Adduction is motion toward the midline of the body represented by arrow 40 in FIG. 1; abduction is motion away from the midline of the body as represented by arrow 41. As shown in FIG. 2, inversion is movement of the foot toward the midline of the body represented by arrow 42 whereas eversion is movement of the foot away from the midline of the body as represented by arrow 43.

Complex motions called "pronation" and "supination" include motions with respect to the ankle, subtalar and midtarsal joints. Pronation includes dorsiflexion, abduction and eversion; supination includes plantar flexion, adduction and inversion. During pronation, dorsiflexion is prominent at the ankle joint, eversion at the subtalar joint and abduction at the forefoot or phalanges 21; during supination, plantar flexion is prominent at the ankle joint, inversion at the subtalar joint and adduction at the forefoot.

In general terms, the optimal anatomical position for a rear foot is a "referenced neutral position" that exists when the subtalar joint 32 is in its neutral position and the forefoot has been locked against the rear foot. The subtalar joint neutral position is defined as the position of the subtalar joint 32 where the joint is congruent (i.e., the talus 26 and calcaneus 27 are on top of one another and the talus 26 and navicular 25 are congruent) and a bi-section of the lower one-third of the leg creates an angle with a bi-section of the posterior portion of the calcaneus 27. Ideally this occurs when the angle is about 3° to 4° varus (i.e., a fixed position of eversion) with the bi-section of the posterior portion of the calcaneus. The forefoot is locked against the rear foot by applying an upward force against the fourth and fifth metatarsal heads.

Many individuals have certain anatomical deformities of the forefoot. Two of these deformities, called "forefoot varus" or "forefoot valgus", effect foot position during walking or running (i.e., through the gait cycle). Referring to FIG. 4A, if the rear foot 44 is in the referenced neutral position and there are no deformities in the forefoot 45, the foot rests on a horizontal surface. If an individual walks with an uncorrected pronated rear foot, over time the individual's foot anatomy will change. When the rear foot is manipulated to a position at which the subtalar joint is in its neutral position, the plantar surface of the forefoot 45 will rotate upward at the body midline as shown in FIG. 4B. This is called "forefoot varus." If the individual walks with an uncorrected supinated rear foot, the lateral side of the metatarsals 22 will rotate upward when the foot is moved to the referenced neutral position as shown in FIG. 4C. This is "forefoot valgus." If an orthotic footbed does not support the forefoot when the individual has forefoot 45 varus or valgus, then during the gait cycle the foot will pronate for varus and supinate for valgus. These characteristics are called "late stage pronation" for varus and "late stage supination" for valgus. If the condition exists, the orthotic insert is not controlling the foot through the whole gait cycle. Each characteristic introduces misalignment and stress to the kinetic chain from the ankle through the knee to the hip.

Figure 5B:
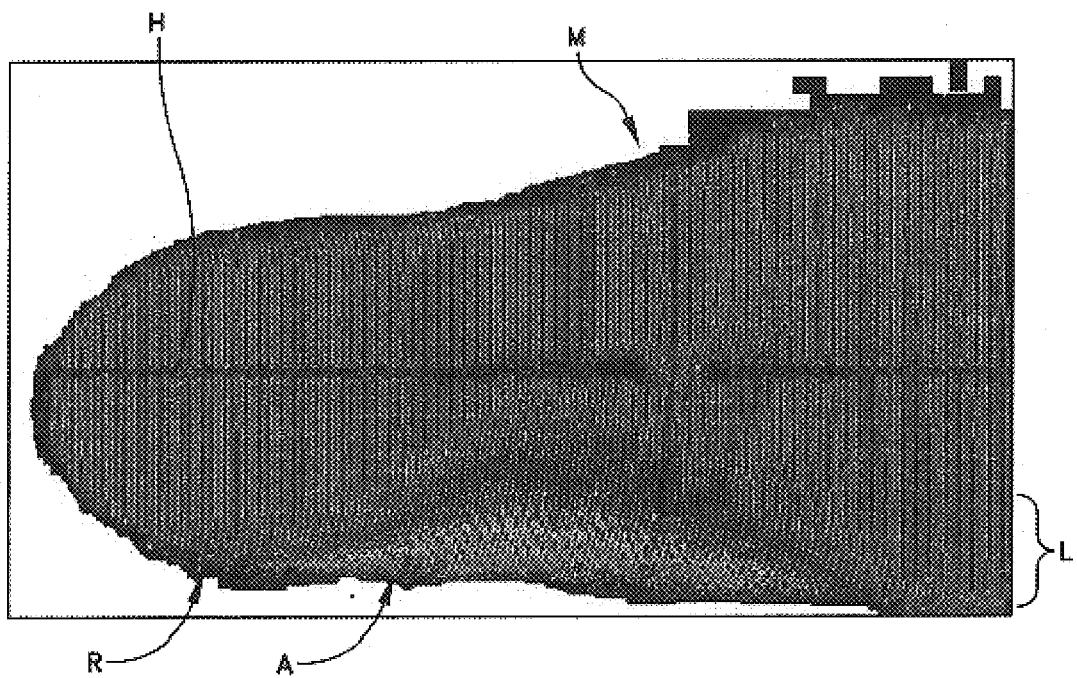

FIG. 5A is a scan of an individual's right foot in the semi-weight-bearing condition; in FIG. 5B the foot is in the full weight-bearing condition. Each of these two scans discloses the topography of the bottom of the rear foot R and midfoot M when the foot is support only on a flat surface. More specifically, the flat appearance in the images represents a spreading and flattening of the tissue that allows the calcaneous to move toward the tissue surface eliminating the normal cushioning of the calcaneous. Through the arch A in the midfoot M, the flat appearance represents a lowering of the arch that stretches the plantar fascia and spreads the tissue, a cause of plantar fasciitis. If an individual's foot were scanned in the non-weight-bearing condition, the image would show plantar fascia in a relaxed state and the tissue with a more rounded form. The portion H shown in FIG. 5A is flat with some rounding shown at the lower portion of the heel H. The portion of FIG. 5B with the full weight increases the area of the flat plantar fascia. An observation of the two figures indicates that the arch in FIG. 5A is higher than the arch in FIG. 5B. In a non-weight-bearing condition the arch may be even higher than that shown in FIG. 5A. Further the images show, particularly at the lower right, that there is no loading of the lateral load-bearing column L because again the plantar fascia is flat on the screen. As will become apparent, any orthotic footbed manufactured to the scans shown in FIGS. 5A and 5B will not reposition the foot in the referenced neutral position and will not accommodate any anatomical deformity such as varus or valgus.

Figure 6:
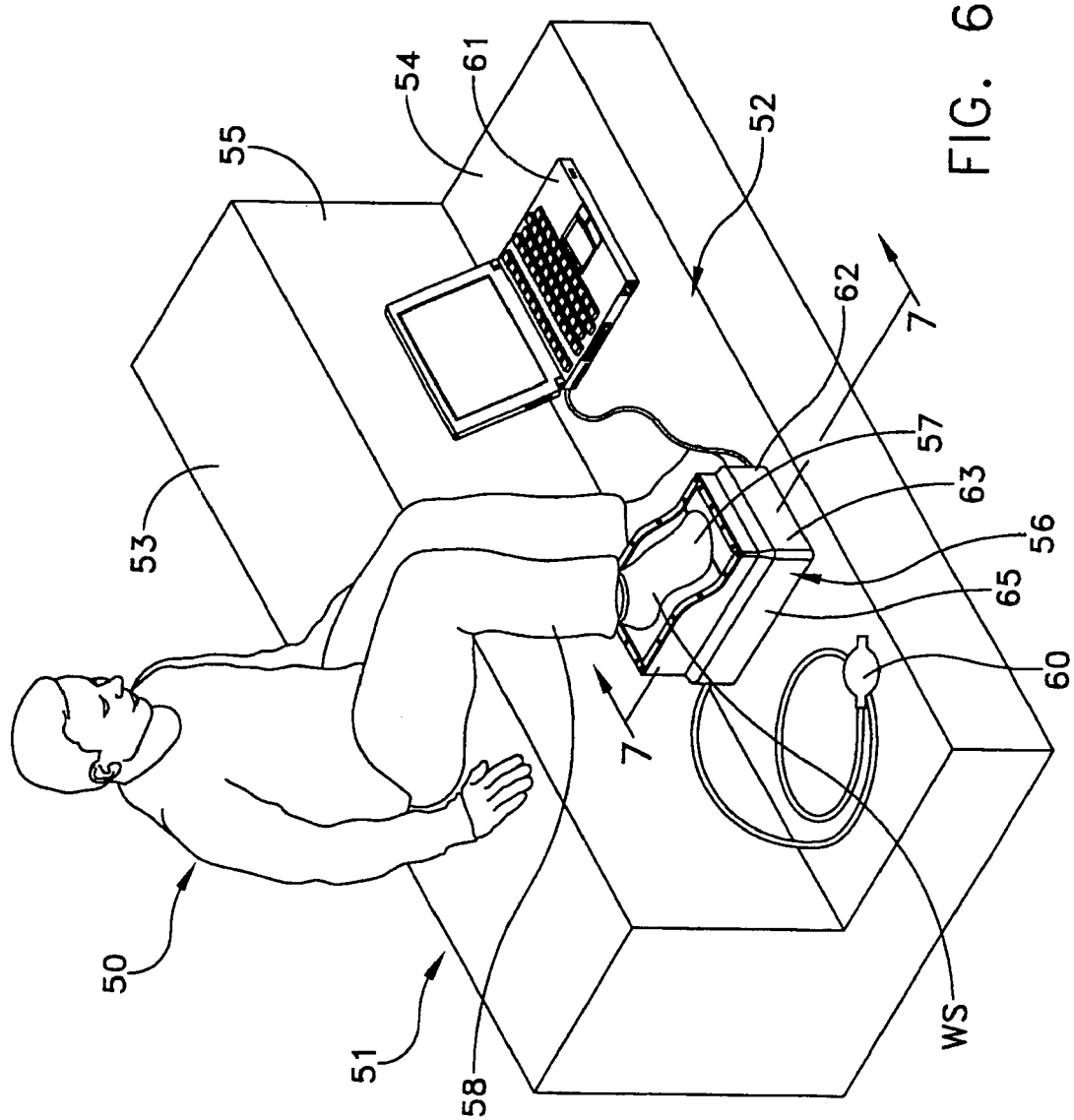
FIG. 6 is a perspective view of an examination site incorporating a foot scanner constructed in accordance with this invention.

In accordance with this invention and as shown in FIG. 6, a practitioner examines a patient 50 in a clean, patient-friendly environment provided at an examination station 51 or other structure that includes a measurement apparatus 52. By way of example, this specific examination station 51 includes a bench 53 at a seating height above a platform 54 determined by a riser 55 selected to allow the patient 50 to sit comfortably with both feet on the platform 54. The platform 54 is elevated above a floor to be at a good working height for the practitioner. The measurement apparatus 52 includes a foot scanner 56 that, as described later, has the properties of an air cushion.

During the measurement process, a practitioner locates the foot scanner 56 under one foot, the right foot 57 in FIG. 6. The foot 57 rests on the top of the foot scanner 56 in the semi-weight bearing condition. The measurement apparatus 52 additionally includes an air pump 60 and a computer-aided control system 61, such as can be implemented by a laptop computer or other means. As will be described, the air pump 60, the control system 61 and the foot scanner 56 interact to produce the measurements of this invention.

The Measurement Apparatus

Referring now to the specific embodiment of FIGS. 6 through 10, the foot scanner 56 comprises a housing 62 with a front wall 63, a rear wall 64 and left and right side walls 65 and 66 respectively. The walls support a bottom shelf 67 and a parallel upper shelf 70 thereby to define an internal equipment compartment 71. The upper shelf 70 comprises a central transparent portion in the form of a transparent plate 72 supported by a peripheral frame 73 attached to the walls 63 through 66. The equipment compartment 71 houses a commercially available three-dimensional laser scanner 74 that connects to a power supply 75 and to the control system 61. In this particular embodiment that scanner 74 is a 3D Digital RealScan USB Model 200 laser scanner manufactured by a 3D Digital Corp. of Danbury, Conn. When the control system 61 initiates a scan, the laser scanner 74 generates a thin linear beam that traverses the transparent plate 72 and converts light returned from any reflective surface in a programmable range above the transparent plate 72 to sensors that produce signals corresponding to the distances from a reference on the laser scanner 74 to the reflecting surfaces. The laser scanner converts these signals into an array of data readings as known in the art.

More specifically, the upper surface of the transparent plate 72 is considered to define an X-Y, or reference, plane 76. Each data reading corresponds to a specific location on reference X-Y plane over the extent of the transparent plate 72; i.e., an array of locations with spacings that can be less than 0.1 mm. The data reading for each point in the array represents the Z-axis, or vertical, distance from the laser scanner 74 to the reflecting surface at that X-Y location. As the laser scanner 74 and transparent plate 72 have a constant separation, the laser scanner 74 can readily convert each reading to represent the distance from the reference plane 76 to the reflecting surface that, in accordance with this invention, is a distance corresponding to the distance from the reference plane 76 to a corresponding location on the bottom of the foot. Thus the laser scanner 74 obtains an array of measurements representing the distance between the reference plane 76 and an array of positions on the bottom of at least the rear foot portion, and preferably of the rear foot and midfoot portions of the foot 52.

Figure 9:
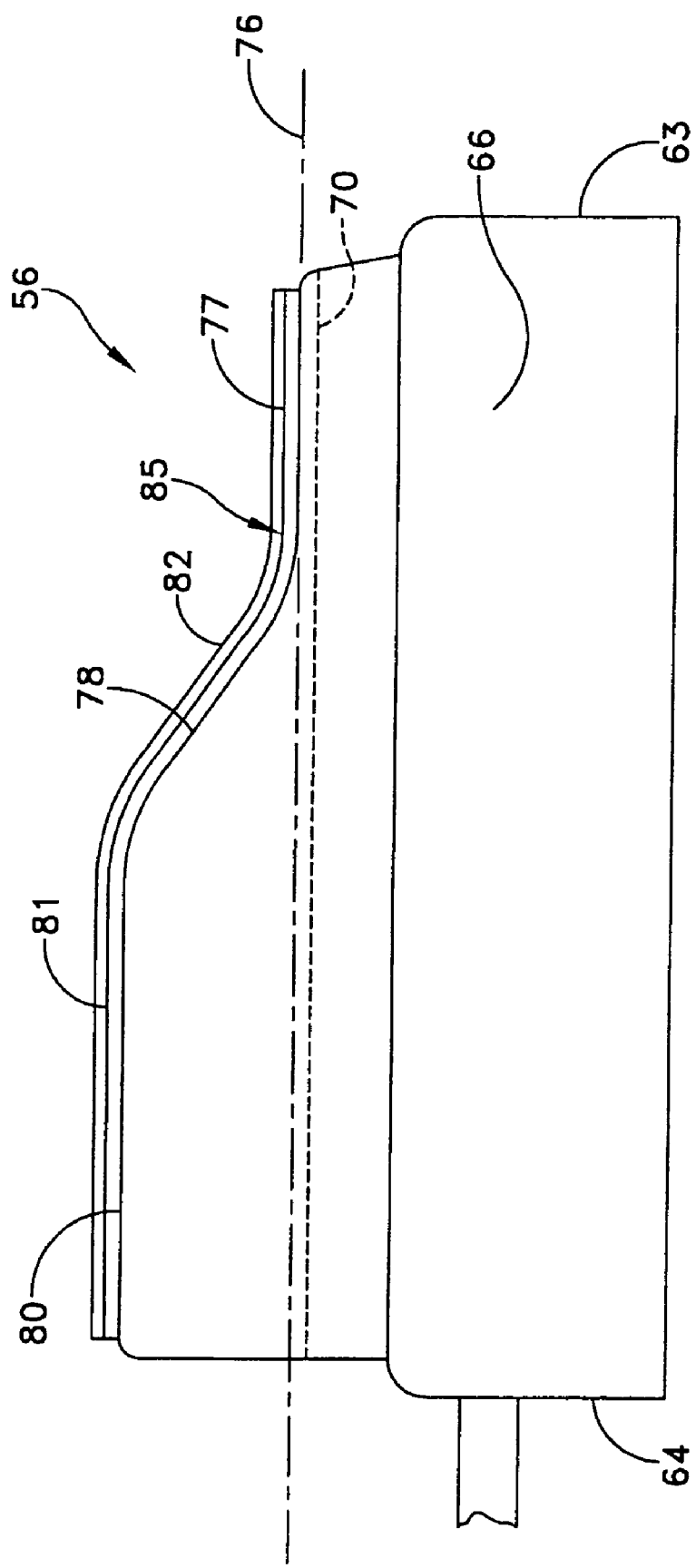
FIG. 9 is a plan view of a portion of a side wall shown in FIGS. 7 and 8.

As previously stated, the foot scanner 56 has the property of an air cushion. Incorporating this property enables the foot scanner to capture pneumatically the patient's foot with the rear foot in the referenced neutral position, with the forefoot supported on the reference plane and with the rear foot floating. To obtain this property, the foot scanner 56 includes portions of side walls 63 and 64 that extend vertically above the upper shelf 70 to an upper edge. Each side wall has the same configuration, so FIG. 9 depicts an upper section of the side wall 66 with portions of the front wall 63 and rear wall 64. A dashed line 76 marks the position of the reference plane at the upper surface of the transparent plate 72 in FIGS. 7 and 8. Still referring to FIG. 9, the upper end of the side wall terminates at a front upper edge portion 77 that is coplanar with the reference plane 76. A ramp upper edge portion 78 rises from the front upper edge portion 77 to a rear upper edge portion 80 that extends at a constant height to terminate at the rear wall 64. These upper edge portions, along with the upper edge portions of the front and rear walls 63 and 64, constitute a support for a thin, flexible, impermeable membrane 81.

In the specifically disclosed embodiment, a frame 82 clamps and seals the periphery of the membrane 81 to the upper edges of the front and rear walls 63 and 64 and to the upper edges 77, 78 and 80. Those portions of the membrane 81 between the ramp and rear upper edge portions 78 and 80 are not stretched; rather they are relaxed. The portion of the membrane 81 between the front upper edges portions 77 is placed under a slight tension. As a result, the flexible membrane 81, upper shelf 70 and walls 63 through 66 define a variable volume, sealed chamber 83 above the reference plane 76 wherein operation of the air pump 60 expands the volume by increasing the pressure within the chamber 83 thereby stretching the membrane 81. During expansion the volume coextensive with the ramp and rear upper edge portions 78 and 80 will tend to expand before the volume coextensive with the front upper edge portion 77.

Figure 10:
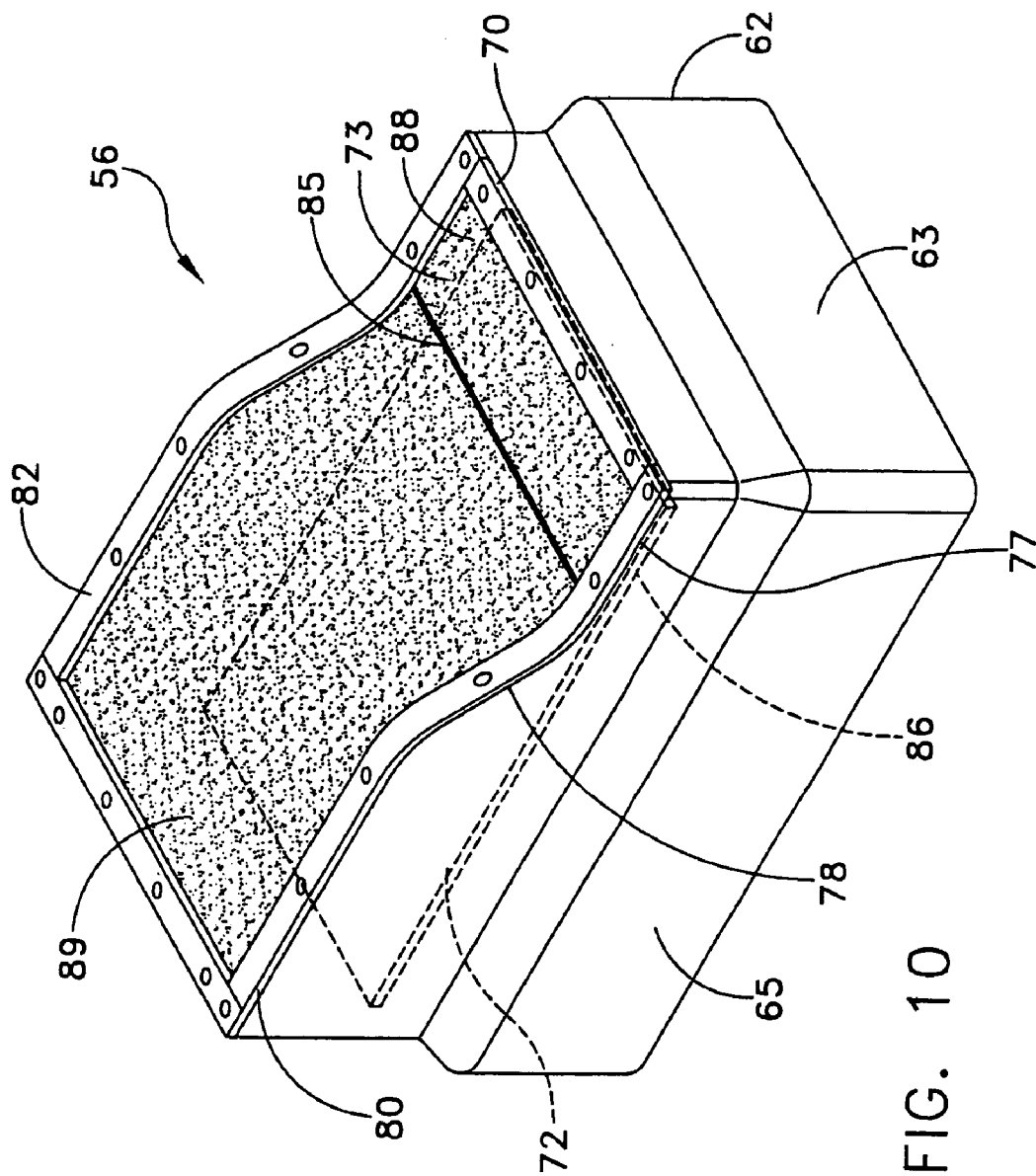
FIG. 10 is a front perspective view of a foot scanner of FIG. 6.

As previously indicated, the top surface of the transparent plate 72 acts as the reference plane 76. The measurement apparatus 52 has an additional reference for aiding the practitioner's placement of a patient's foot. Referring particularly to FIGS. 9 and 10, this second reference takes the form of a line 85 extending across the top of the flexible membrane 81 so it is visible to the practitioner. This line 85 is parallel to the front edge 63 and positioned to the rear of the front edge 86 of the transparent plate 72 and corresponds to the boundary between the stretched and relaxed portions of the flexible membrane 81.

Figure 11:
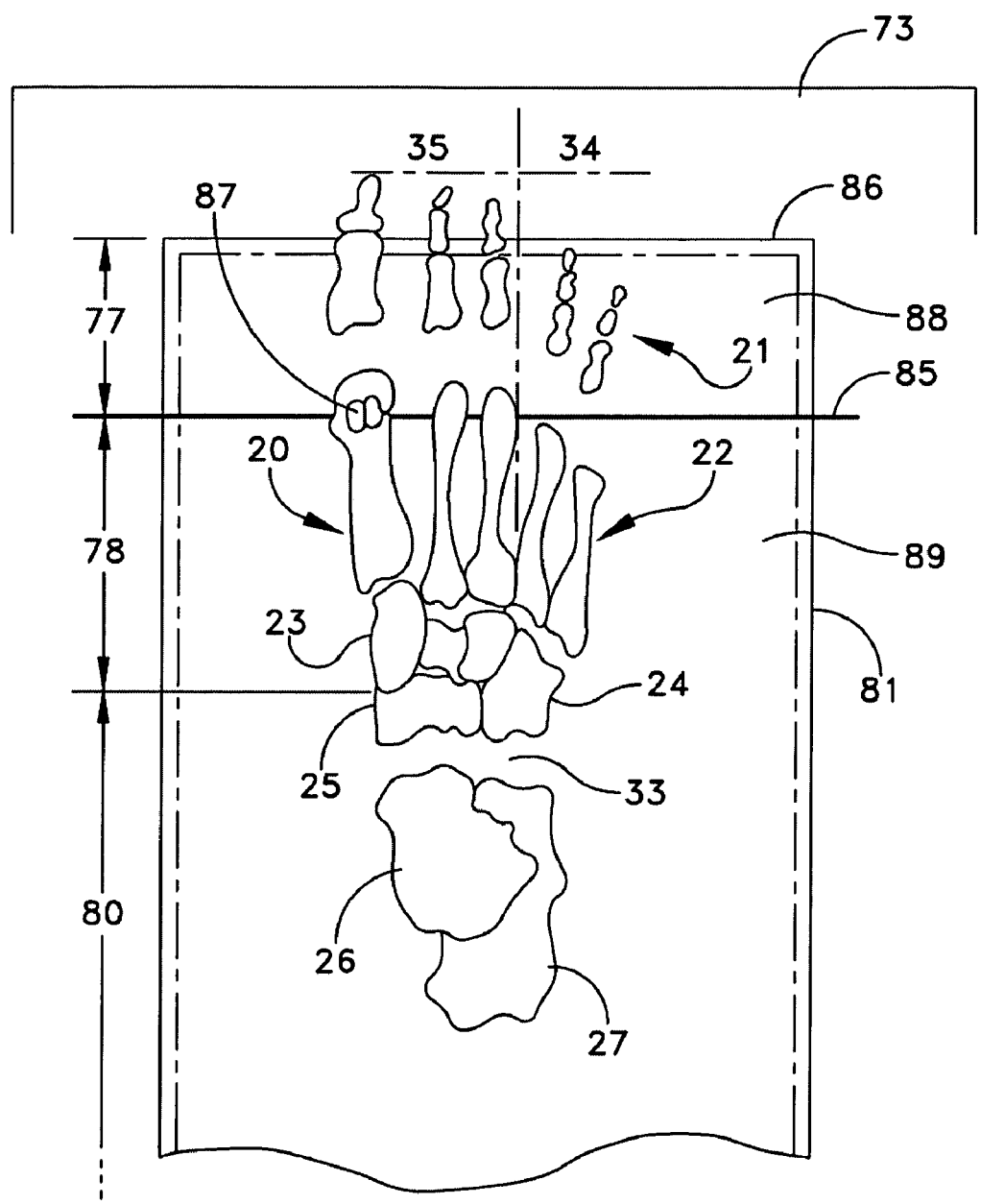
FIG. 11 is a top view of a portion of the foot scanner of FIG. 10 with superimposed skeletal anatomy of a right foot.

Referring now to FIGS. 10 and 11, in one particular embodiment, the line 85 is about 63.5 mm from the front wall 63 and about 12.5 mm behind a front edge 86 of the transparent plate. The practitioner positions an individual's foot so that the first-metatarsal-phalanges joint 87 (i.e., the big toe joint) is centered on the line 85. With this positioning the portion 88 of the inflated membrane 81 between the front upper edges 77 supports the forefoot, particularly the phalanges 21.

The ramp upper edge portions 78 assure that corresponding portion 89 of the membrane 81, when inflated, supports the foot between the metatarsals 22 from the metatarsal heads through the cuneiform 23. This allows the air cushion to dorsiflex the $4^{th}$ and $5^{th}$ rays of the metatarsals so that the forefoot and midfoot lock against the rear foot at midtarsal joint 33. It has been found that this result can be attained when the ramp upper edge portions 78 orient the membrane portion 89 with a slope with 5 cm. rise over a 10 cm. run. The total length of the sloped surface in this embodiment, including curved transitions at either end, is about 12 cm.

The upper edges 80 extend to the rear wall 64 for a distance that is dependent upon the size of feet to be accommodated. In one particular embodiment the distance from transition between the ramp upper edge portions 78 and rear wall 64 is about 25 cm to provide a measurement capability of up to a size 20 male shoe.

Figure 7:
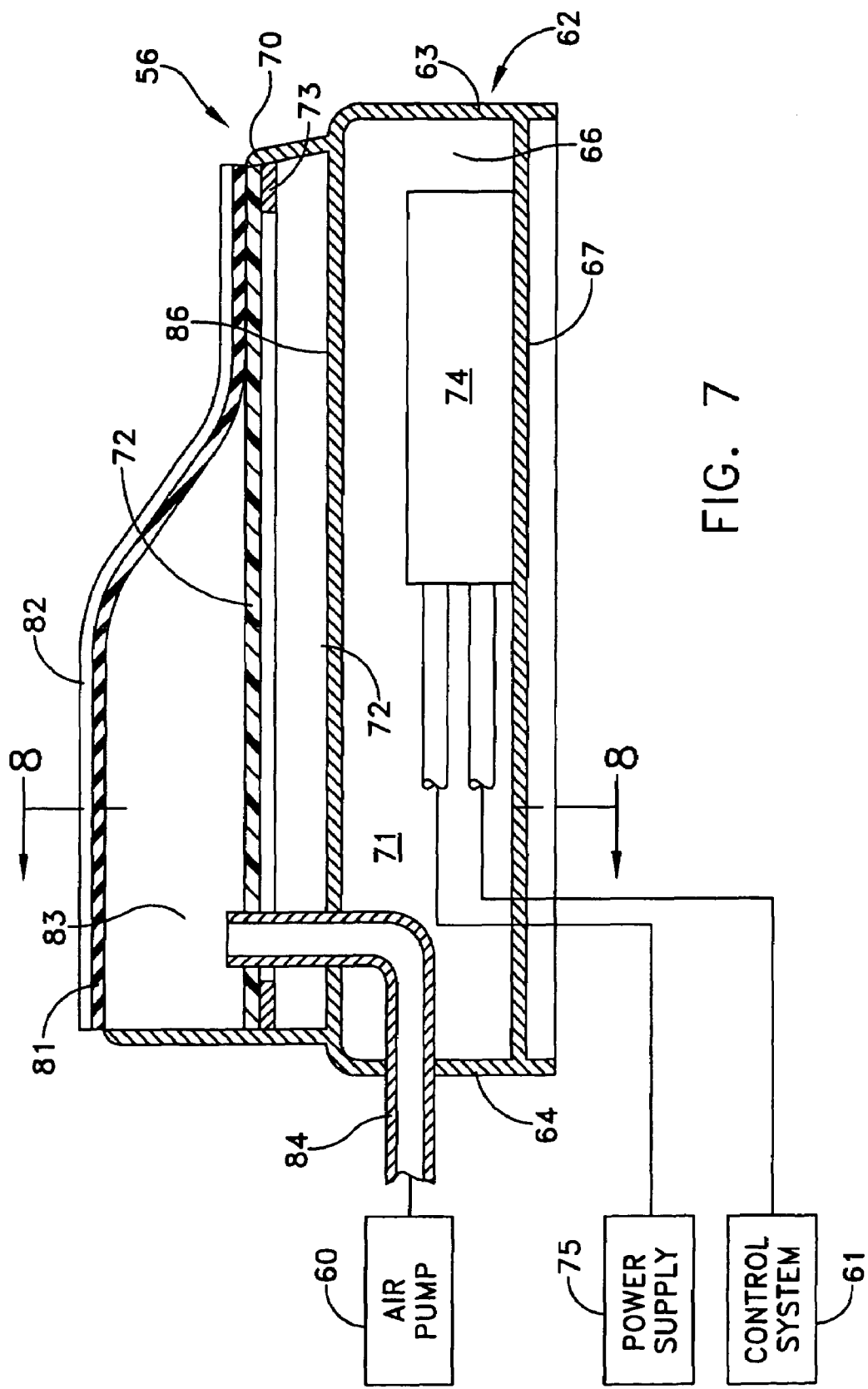
FIG. 7 is a longitudinal cross-section along lines 7-7 through the foot scanner of FIG. 6.
Figure 8:
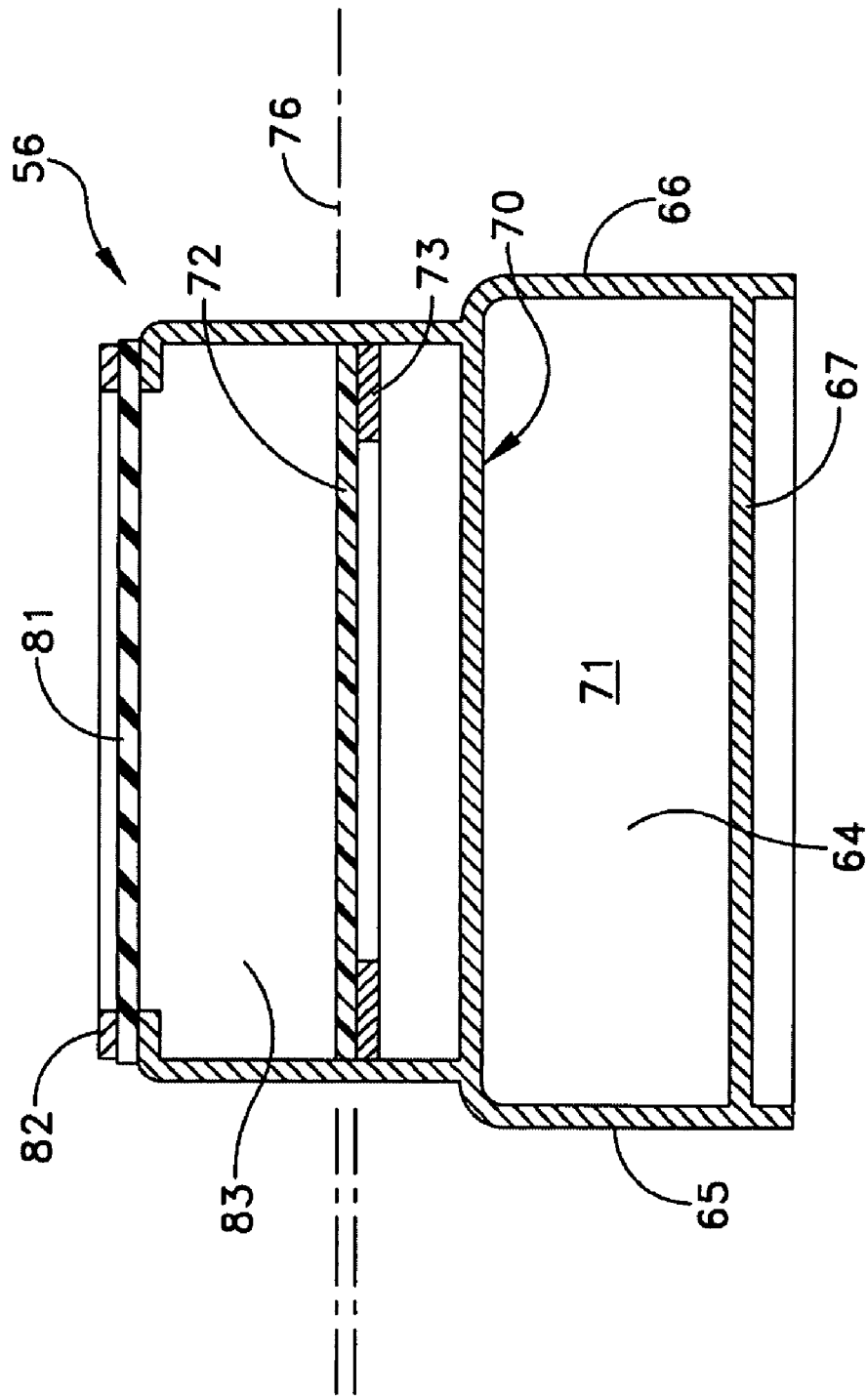
FIG. 8 is a cross-section along lines 8-8 of FIG. 7.

Referring again to the specific embodiment of FIGS. 6 and 7, the air pump 60 connects through a fitting 84 into the chamber 83. Although not shown in detail, in one embodiment the air pump 60 has a conventional one-way pumping action and pressure release valve. With the pressure relief valve closed, the air pump 60 pumps air into the chamber 83 and increases the chamber volume. When the pressure relief valve is opened, air in the chamber 83 escapes until the internal pressure reaches atmospheric pressure.

When the chamber 83 is deflated, the weight of the patient's foot displaces the membrane 81 toward the transparent plate 72 and reference plane 76, particularly portions under the calcaneus 27 that can come to rest on the transparent plate 72.

Figure 12:
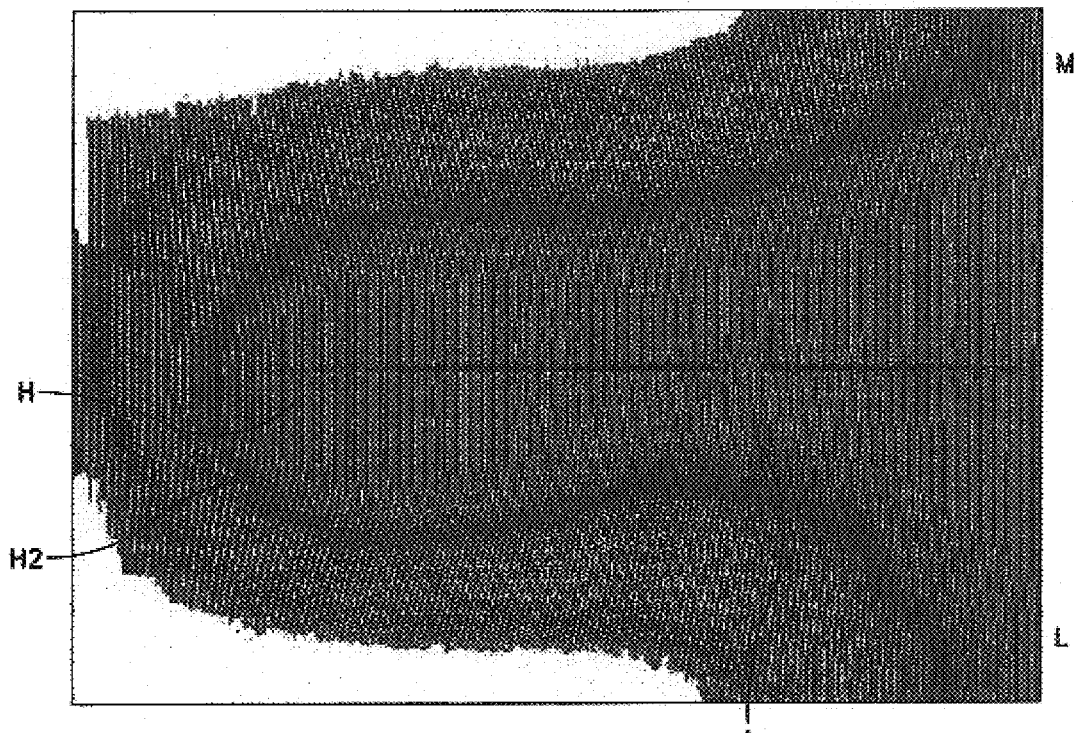
FIG. 12 depicts a scan of a right foot in the semi-weight-bearing condition when the foot scanner is deflated.

FIG. 12 depicts a scan that is produced when the individual's right foot is positioned as shown in FIG. 10 with the air chamber deflated. In this view the reflections are from the bottom surface of the membrane 81. The red area in the center of the heel portion H is more rounded than is shown in either of FIG. 5A or 5B. The membrane 81 is slightly stretched when the heel of the foot rests on the reference plane 76, so that portion around the heel H begins to cup the heel as shown at H2. Further the membrane has begun to fill the arch A. This cupping and filling are represented by the blue color. The green band represents that portion of the membrane that is extending away from the heel and back toward the structure turning to a purplish color. The green and purple areas of the scan are irrelevant.

When a foot is properly positioned as shown in FIG. 11 and manipulated to the referenced neutral position, increasing the air pressure in the chamber 83 forces the flexible membrane 81 into contact with the entire plantar fascia surface of the foot. As the material of the membrane 81 is thin and compliant, the underside of the membrane 81 essentially contains and compresses the tissue on the bottom of the rear foot to support the coextensive portions of the plantar fascia and foot structure.

The material of the membrane is also selected to optimize laser reflection so that the laser energy from the laser scanner 74 is reflected back to sensors in the scanner to provide an array of measurements that correspond to the distance from the reference plane at the top of the transparent plate 72 to the underside of the flexible membrane 81. This reading is a good approximation of the height to the plantar surface and thickness of the membrane 81 can be accommodated in the generation of data. As shown in FIG. 6, a patient may don a thin white sock WS to improve the reflection characteristics during the scanning operation. Still other reflectivity enhancing features could be incorporated in the scanner as, for example, the deposit of a highly reflective flexible film on the surface of the membrane 81 facing the laser scanner 75.

Figure 13:
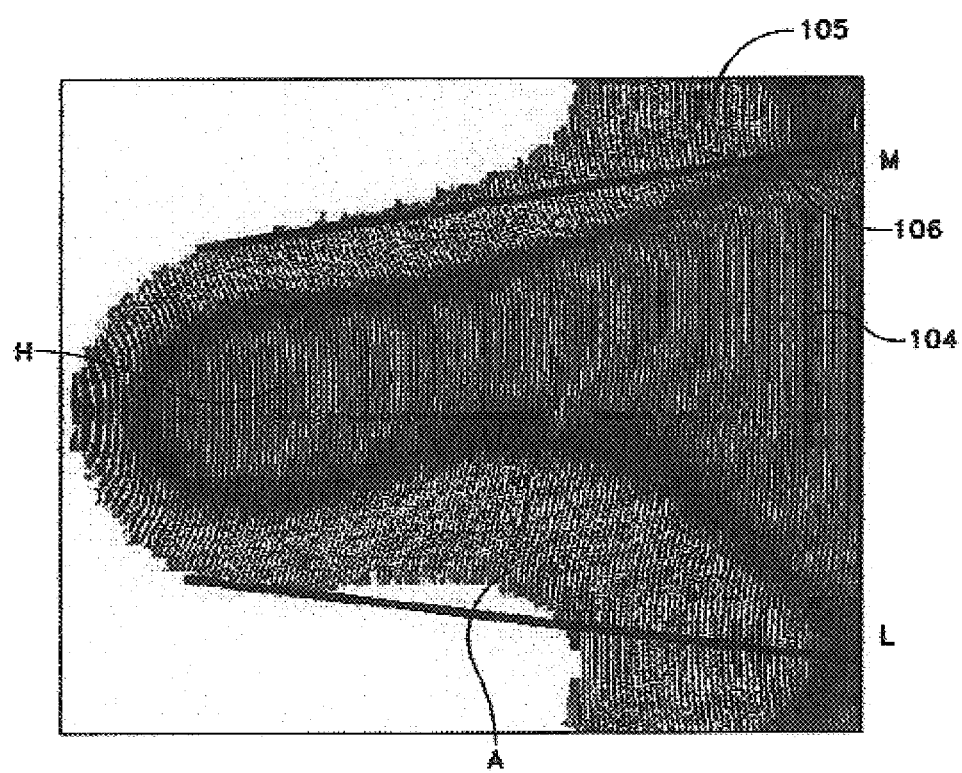
FIG. 13 is a scan obtained from the foot scanner in the semi-weight-bearing condition when the foot scanner is inflated.

FIG. 13 depicts a scan that is produced when the foot is captured in the referenced neutral position in the foot scanner 56 in the chamber 83 inflated so the forefoot and midfoot are locked against the rear foot and the heel H is elevated above being the reference plane 76. In one specific embodiment the heel elevation is two or three millimeters. Comparing FIGS. 12 and 13, the heel is well rounded in FIG. 13. The arch becomes narrower from left to right. The lateral column is now loaded as shown at L because the blue color indicates a slight lift of the bottom of the foot that is consistent with varus. There is no change in the medial column. The lateral arch is fully supported and the calcaneus, navicular and cuboid are supported to be congruent.

Figure 14A:
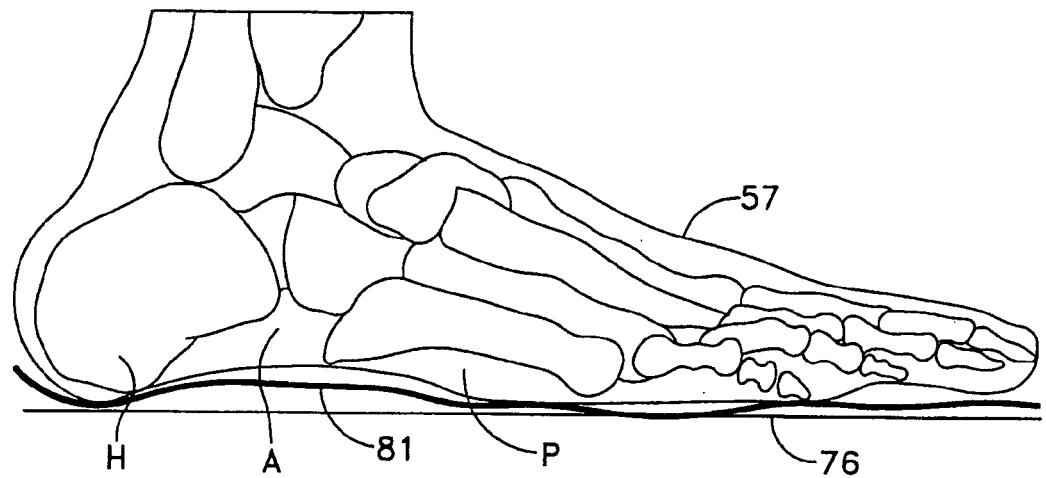
FIGS. 14A and 14B are side views of a right foot looking at the lateral load-bearing column positioned on the foot scanner of FIGS. 6 through 10.
Figure 14B:
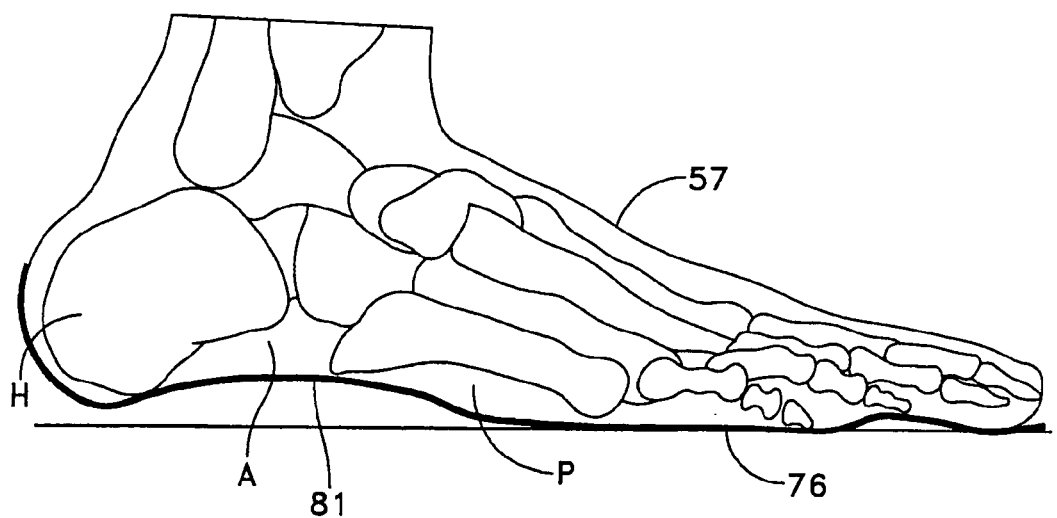
Figure 15A:
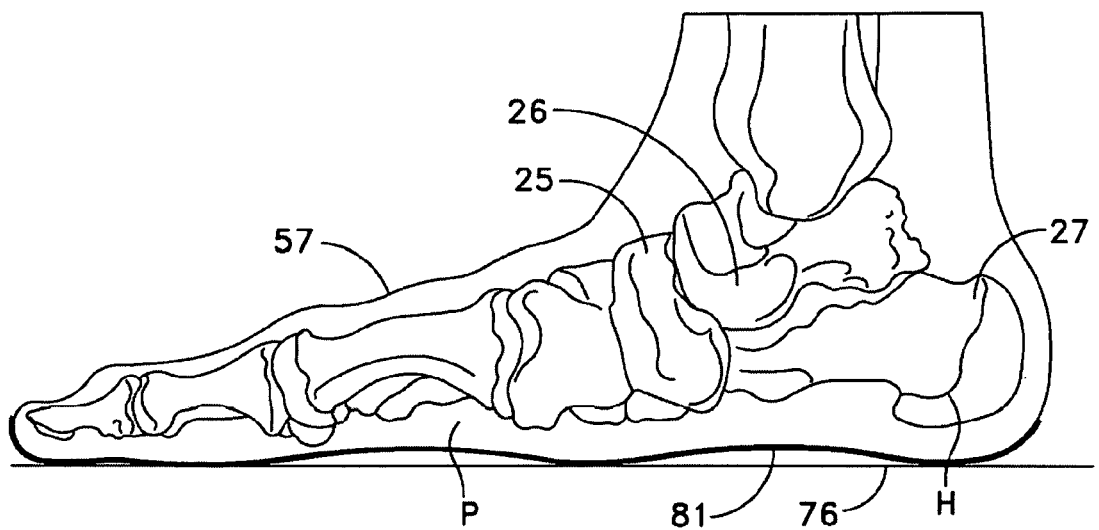
FIGS. 15A and 15B are side views of a right foot looking at the medial dynamic column positioned on the foot scanner of FIGS. 6 through 10.
Figure 15B:
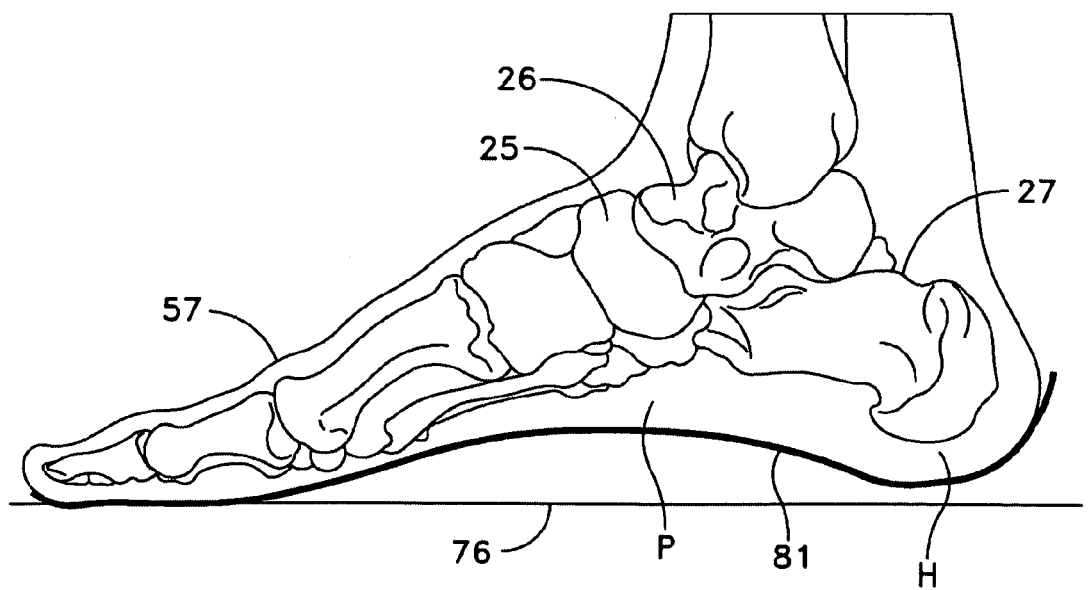

FIGS. 14A and 14B illustrate the impact the air cushion has on the foot alignment, particularly with respect to the lateral load-bearing column 34. FIGS. 15A and 15B depict the effect on the medial dynamic column 35. FIGS. 14A and 15A depict a foot 57 resting on the reference plane 76. The membrane 81 is shown with the heel H resting at the reference plane. The arch is flattened. Moreover, FIG. 15A depicts a flattened arch that can occur if a foot is improperly supported over a long period of time. When this occurs, the spring ligaments stretch and the joint formed by the navicular 25, talus 26 and calcaneus 27 opens.

FIGS. 14B and 15B depict the position of the foot 57 relative to the reference plane 76 when the air pressure increases so the membrane 81 elevates heel H slightly above the reference plane. Now the membrane 81 conforms to the bottom of the foot. The pressure in the membrane 81 causes the membrane to hold the foot into an appropriate referenced neutral position. It also causes the membrane 81 to contain and compress the tissue and support the plantar fascia and structure. The loading of the lateral load-bearing column by the membrane 81 locks the forefoot and midfoot against the rear foot, as previously described. In this case the arch is better defined as can be seen by reference to FIGS. 14A and 14B. Moreover, as shown in FIGS. 15A and 15B, the navicular 25, talus 26 and calcaneus 27 come into alignment in FIG. 15B and the arch is significantly elevated over that which exists without this support. Again, this is produced by the pressure in the chamber 83 and the resulting force that the membrane 81 exerts against the tissue, plantar fascia and structure P. As will now be apparent, if an orthotic insert matches the configuration of the membrane 81 as shown in FIGS. 14B and 15B, that orthotic insert will support the patient's foot in his or her footwear correctly.

Patient Examination and Scan

With this background of the construction and operation of the foot scanner 56, it will now be possible to describe a measurement process by which a practitioner acquires the information about the patient's foot without the need for a cast. The process begins by initiating a session as represented by step 90 in FIG. 16. A "session" can include a procedure for a single patient or multiple patients seen in some time period, such as a day.

The first procedure, as represented by steps 91 and 92, involves obtaining and storing patient information. More specifically, the practitioner interviews the patient (step 91) to obtain bibliographic information, medical information particularly related to foot evaluation, lower body alignment, gait evaluation, footwear evaluation and other relevant information. FIG. 17 depicts a sample evaluation form for entering patient information on a sheet. As an alternative the evaluation form could be a template displayed on a computer screen for being filled out by the practitioner.

Two items that are of interest with respect to this invention are (1) the arch height entry A and the varus/valgus entries at V. Measurements of the arch height in a near non-weight-bearing condition are useful in establishing an upper limit of the scanning range for the laser scanner 74 in FIG. 7. A near non-weight bearing condition is achieved by having the patient sit and by lifting the leg until the foot just touches a surface. These measurements generally are taken with the patient's foot off the scanner 56. The difference in the measured arch heights between the near non-weight-bearing condition and full weight-bearing condition provides an indication of materials to be used in the orthotic. The full weight-bearing measurement can be taken when the patient stands on the platform 54. Measurements of any varus or valgus of a foot alert laboratory personnel of some special steps to be taken in the production of the orthotic insert as described later. Once the patient interview of step 91 in FIG. 16 has been completed, the practitioner uses the control system 61 to open a patient file and enters the information in step 92.

Figure 16:
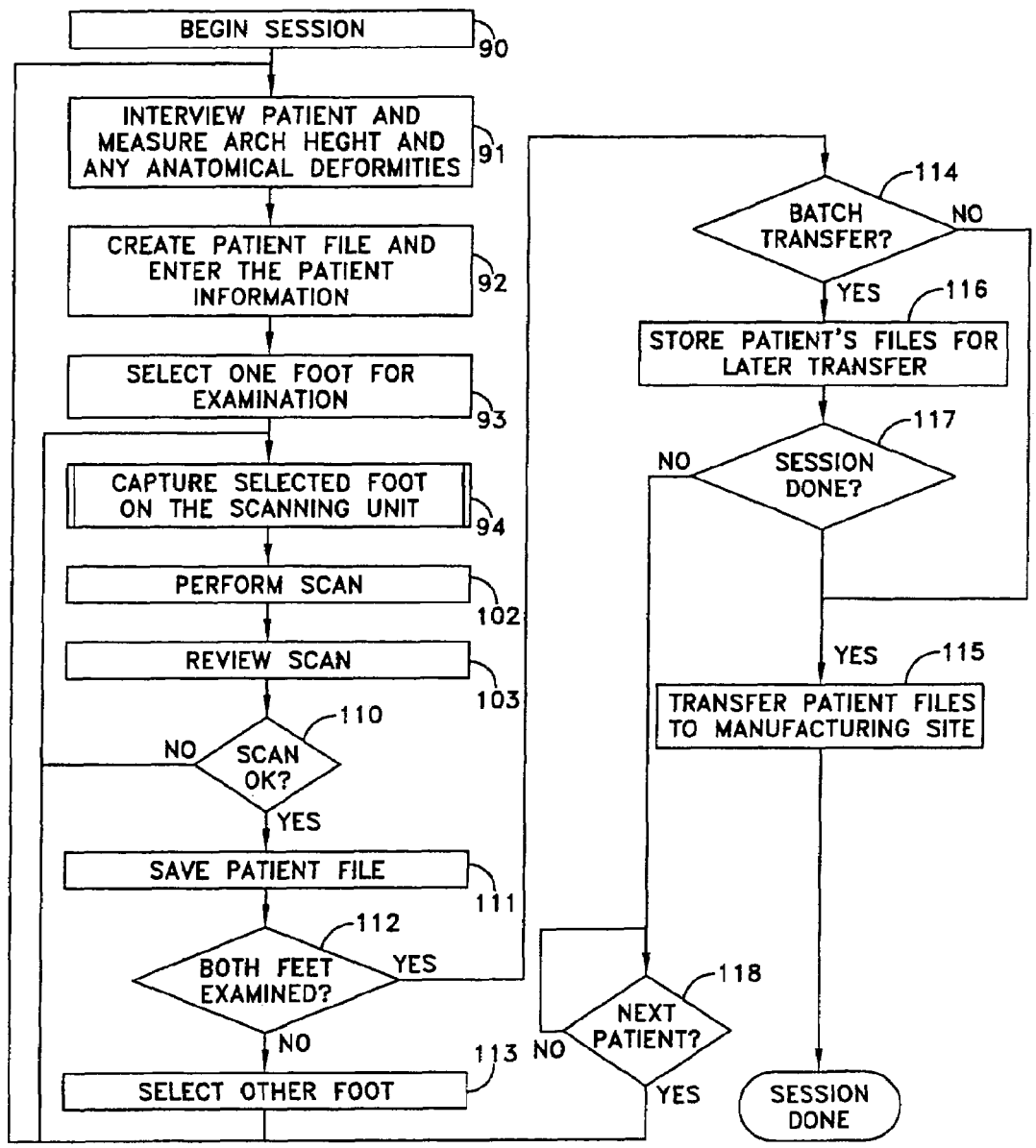
FIG. 16 is a flow chart that depicts the patient measurement process.
Figure 18:
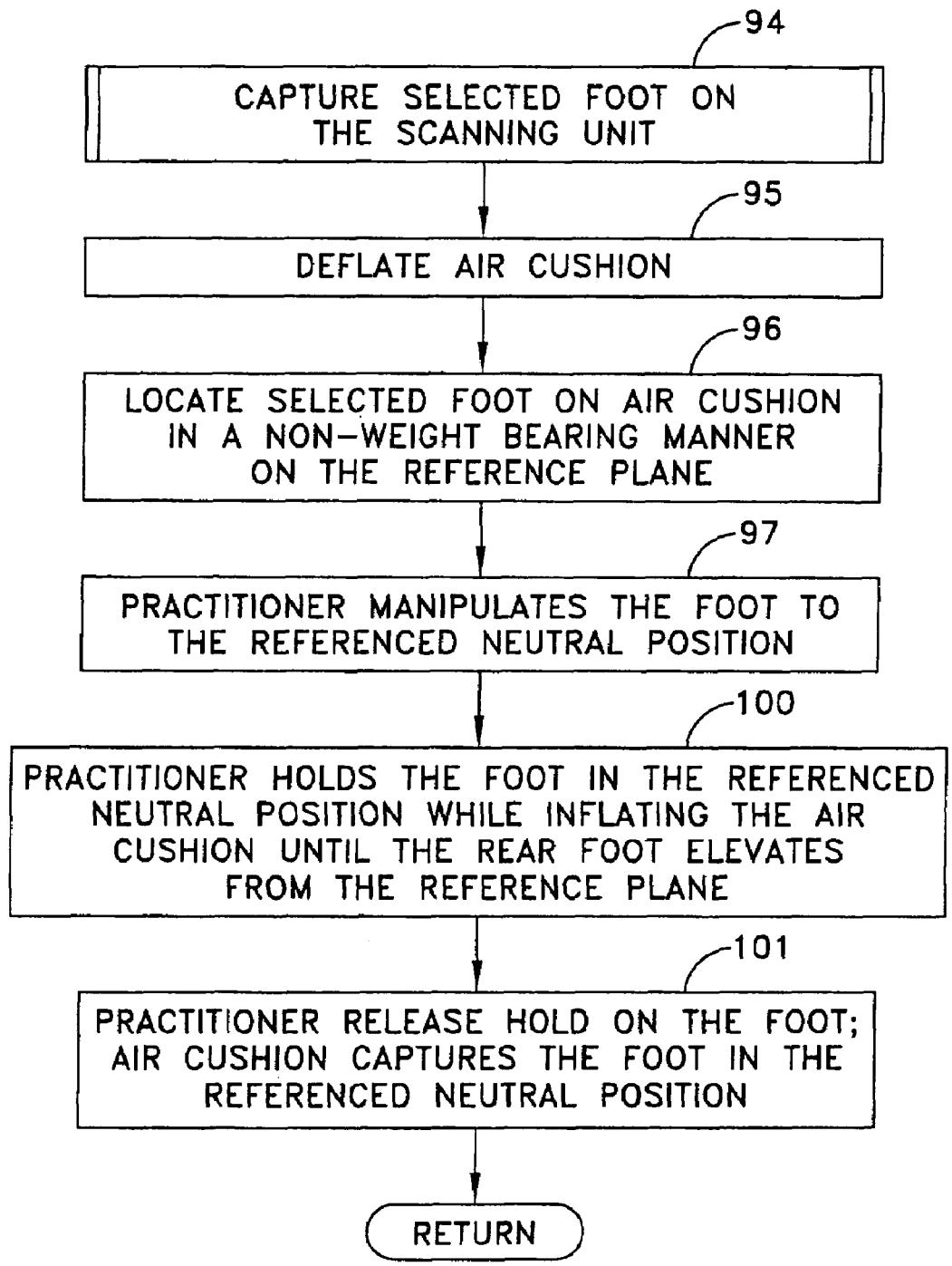
FIG. 18 is a detailed flow chart of a foot capture procedure FIG. 16.

Step 93 in FIG. 16 represents the process by which the practitioner selects one foot for evaluation by a procedure 94 shown in greater detail in FIG. 18. More specifically, the procedure 94 captures the selected foot in a referenced neutral position with the forefoot and midfoot locked against the rear foot. Assuming that the right foot is selected, the practitioner implements a process represented by step 95 in FIG. 18 for deflating the air cushion or chamber 83, typically through a pressure release valve associated with the air pump 60. Step 96 represents the process by which the practitioner locates the selected foot (i.e., the right foot 57 in this example) on the membrane 81 as previously described. As the air pillow is deflated, the foot 57 lies on a reference plane defined by the transparent plate 72 in an orientation with the first metatarsal phalanges joint 87 on the line 85 and the foot centered on the membrane 81.

Step 97 represents the action of the practitioner in manipulating the knee and foot to move the foot to the referenced neutral position. Basically the practitioner places his or her fingers on opposite sides of the talar head and the foot and palpates the bump on either side until the bumps are even or congruent. When this occurs, the talus 26 and the navicular 25 in FIG. 1 are congruent and the subtalar joint 32 is in a neutral position. This is an ideal position. As previously indicated, however, it may not be possible to move a foot of some patients to this neutral position without discomfort. In that situation the practitioner may elect to move the foot only partially toward this referenced neutral position.

Step 100 represents the action of the practitioner in holding the foot in this position while operating the air pump 60 to inflate the air cushion while observing the position of the heel. Referring to FIGS. 14B and 15B, as the pressure in the sealed chamber 83 increases, the membrane 81 molds to the plantar fascia surface P over with equal pressure. Moreover, as the membrane 81 has a width that is greater than the width of a foot, the membrane 81 begins to move up along the sides of the foot. When the membrane 81 lifts the heel H off the reference plane 76, the air cushion "captures" the foot in the optimal orientation for a measurement and applies an upward pressure on the lateral column 34 in FIG. 1 to lock the forefoot and midfoot.

Step 101 represents an optional step during which the practitioner may release his or her hold on the patient's foot because the air cushion formed by the membrane 81 and sealed chamber 83 captures the foot in the referenced neutral position. However, the practitioner may desire to hold the patient's knee in a fixed location to avoid any errors that might be introduced into the measurements should the patient move his or her leg over a significant range during even the short interval for the actual scan.

Once the foot is captured, the examination process returns to step 102 in FIG. 16 whereupon the practitioner initiates the scan. Typically the practitioner will use the control system 61. More specifically, the practitioner will initiate an application that causes the laser scanner 74 to scan the transparent plate 72.

As known, a three-dimensional laser scanner can be controlled to provide measurements over a specified range or depth of field. During the measurement the minimum distance to be measured is the distance from the laser scanner to the top surface of the transparent plate 72 (i.e., the reference plane). This is a fixed number that can include as a constant in the control application. The maximum distance is based upon the distance to the top of the arch as measured in step 96 of FIG. 18. Generally, the maximum distance will be set the sum of the distance to the reference plane plus the measured arch height plus 2 or 3 mm to compensate for the elevation of the rear foot above the reference plane by the air pillow while the scan is being made.

Once the scan is completed, which is a matter of only a few seconds, the practitioner displays the scan on the control system 61 for review in step 103. As shown in FIG. 13, this scan includes both relevant 104 and irrelevant 105 information because the laser scanner images the entire bottom surface of the membrane that is coextensive with the transparent plate. A line 106 indicates the boundary between the portions 104 and 105. The relevant portion 104 of the image of FIG. 13 provides the practitioner with a ready check on the validity of the scan. Typically the practitioner will look to see that the scan has a maximum distance at about the center of the heel H and that heel H is presented with a rounded appearance. If the practitioner is not satisfied with the scan, then, as shown by step 110 in FIG. 16, the practitioner recaptures the foot in the procedure 94 and repeats the scan and review processes of steps 101, 102 and 103.

When the practitioner is satisfied the scan, the practitioner saves the scan as a patient file for the selected foot as represented by step 111. If the practitioner needs to examiner the other foot, the procedure passes from step 112 to step 113 for selecting the other foot. Then the practitioner repeats the capture process 94 and the scan and review steps 101, 102 and 103. If both feet have been examined, the practitioner transfers the patient's files to a local or remote manufacturing site.

When the manufacturing facility is local to the measurement apparatus 52 in FIG. 6 each patient's files can be transferred to the local manufacturing site when they are saved. Alternatively, if a plurality of examination stations, like the examination station 51 in FIG. 6, are networked to a common manufacturing site, it may be desirable to save the individual files at the examination station for a periodic transfer, such as a daily transfer, from the examination station to the manufacturing facility site. Referring again to FIG. 16, step 114 represents a process by which the operation passes control to step 115 for transferring patient files to the manufacturing facility and completion of the session. If batch transfers are to be made, such as at the end of a business day, the files are stored locally for later transfer as in the control system 61 or other storage facility at the examination station, as represented by step 116. When the session is then completed, steps 117 and 115 make the transfer of all the patient files to the manufacturing facility. If the time has not arrived for such a transfer, step 118 represents waiting for a next patient examination to begin. Then the process starts at step 91.

Thus, the measurement apparatus 52 at an examination station 51 has the capability, through the use of the air pillow, of capturing an individual patient's foot after the foot has been manipulated to the referenced neutral position by the practitioner. Inflating the air pillow also locks the forefoot and midfoot against the rear foot to accommodate any anatomical deformities, such as valgus and varus. The laser scan records the entire contour of the plantar surface in the rear foot, mid foot and the forefoot to the metatarsal heads in the semi weight-bearing condition. This recording can, as will now be described, be converted into a custom orthotic insert of a medical quality without the need for the use of plaster casts and molds and without the need for subsequent special fittings by the practitioner.

The Manufacturing Site

Figure 19:
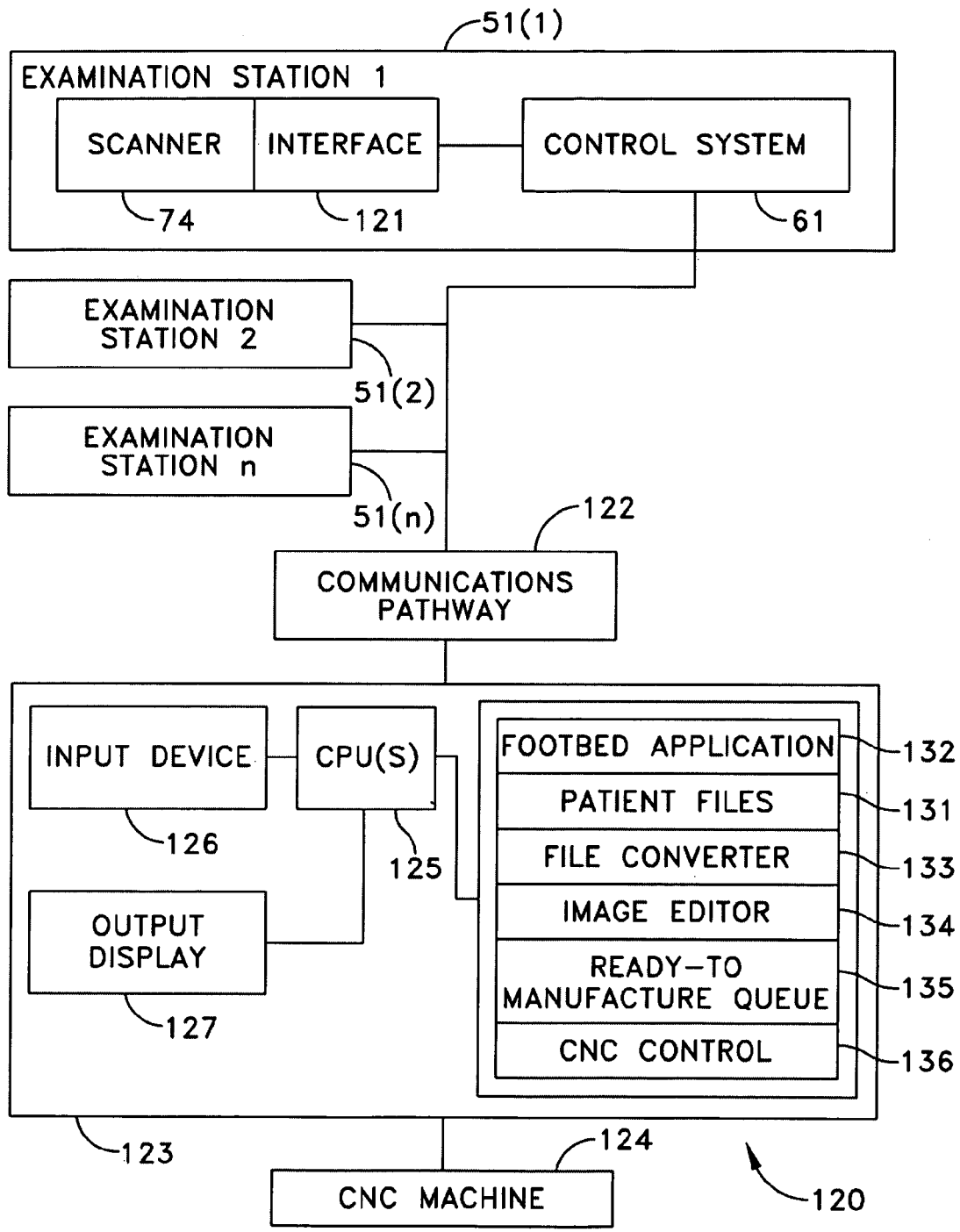
FIG. 19 is a block diagram of a network for interconnecting multiple examination sites such as shown in FIG. 6 with a central manufacturing facility.

FIG. 19 depicts a manufacturing site 120 that connects to the examination station 51(1) along with additional examination stations 51(2) through 52(n). As previously indicated, the examination station 51(1) includes the scanner 74 and the control system 61 and also includes an interface 121. The control system 61, in turn, connects through the Internet, a local network, a wide area network or other communications pathway 122 to the manufacturing facility 120.

The manufacturing facility 120 includes a server 123 and manufacturing apparatus, such as a Computer Numerically Controlled (CNC) machine 124. The server 123 includes one or more CPUs 125 that respond to commands from an input device 126, such as an operator keyboard or other input interface device. A graphics or other display 127 provides information to an operator.

The CPUs 125 also connect to a data storage device 130 The data storage device may be partitioned or divided into files or directories for storing a variety of information. For implementing this invention, the data storage device 130 includes a patient data file storage 131 that is typically managed through a data base manager. This file storage area stores all patient files from all examination stations 51. As will be described in more detail later, the data storage device 130 also includes a footbed application program 132 that provides overall control of the manufacturing facility 120. That is, the footbed application 132 includes those programs or procedures necessary for receiving and storing patient files from one or more examination stations 51 as patient data files. It will also include a scheduling program or procedure of selecting a specific patient file from the patient data files 131 for processing. The footbed application 132 also provides a means for enabling the orderly processing of the patient's files for manufacture of orthotic footbeds. A file converter 133 converts data in patient files into a format that is compatible with the format used at the manufacturing facility 120, if such a conversion should be necessary. An image editor 134 provides a means of removing the irrelevant image portion 105 in FIG. 13 and storing the edited images as a patient control file in a ready-to-manufacture queue 135. A CNC control application 136 in FIG. 19 retrieves patient control 136 to enable the manufacture of the orthotics for a patient.

The Manufacturing Process

Figure 20:
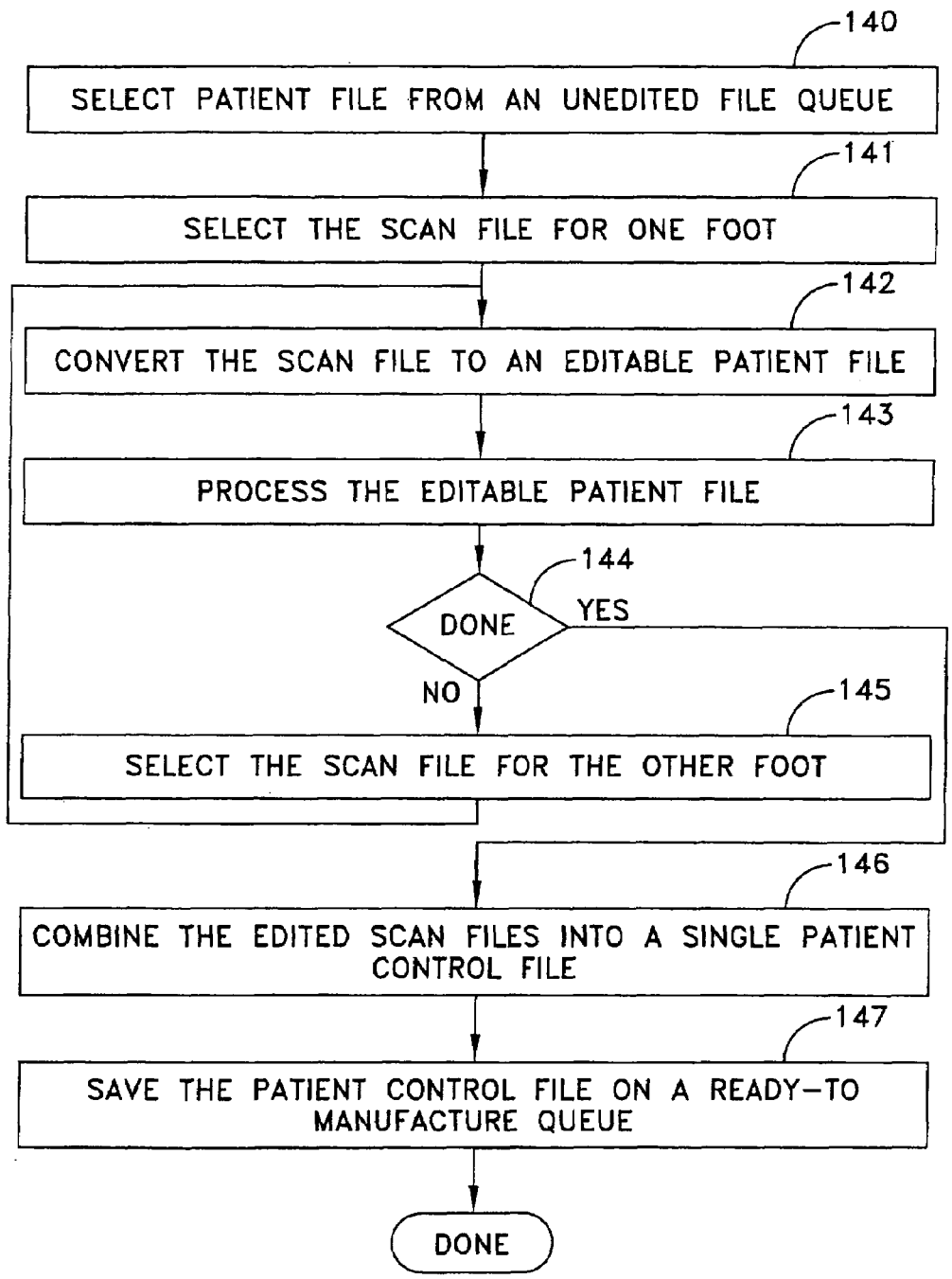
FIG. 20 is a flow diagram of the process for converting scan images into a form for production.

FIG. 20 depicts one possible sequence of steps of the footbed application 132 for editing the images in a patient file to eliminate the irrelevant image portions 105 of FIG. 13. At step 140 in FIG. 20 laboratory personnel select a patient file from an unedited file queue in the patient files 131. The use of such queues in the manner described is well known to those skilled in the art. After selecting one foot in step 141, personnel use step 142 to convert the patient's scan image file into a form for editing automatically. Step 143 represents the process by which the irrelevant portions of the image 105 are eliminated. Graphics applications for performing this function are well known in the art. This produces the image of FIG. 21. After the scan file for the first foot is processed, steps 144 and 145 represent the steps by which the image for the other foot is selected for conversion and edited. Both images are combined at step 146 into a single patient control file. The patient control file contains all the data required for controlling the CNC machine 124 in FIG. 19. Referring to FIG. 20, step 147 represents the process of transferring the patient control file to a ready-to-manufacture queue 135 in FIG. 19 for later transfer to the CNC machine 124 to manufacture the corresponding orthotics.

Figure 22:
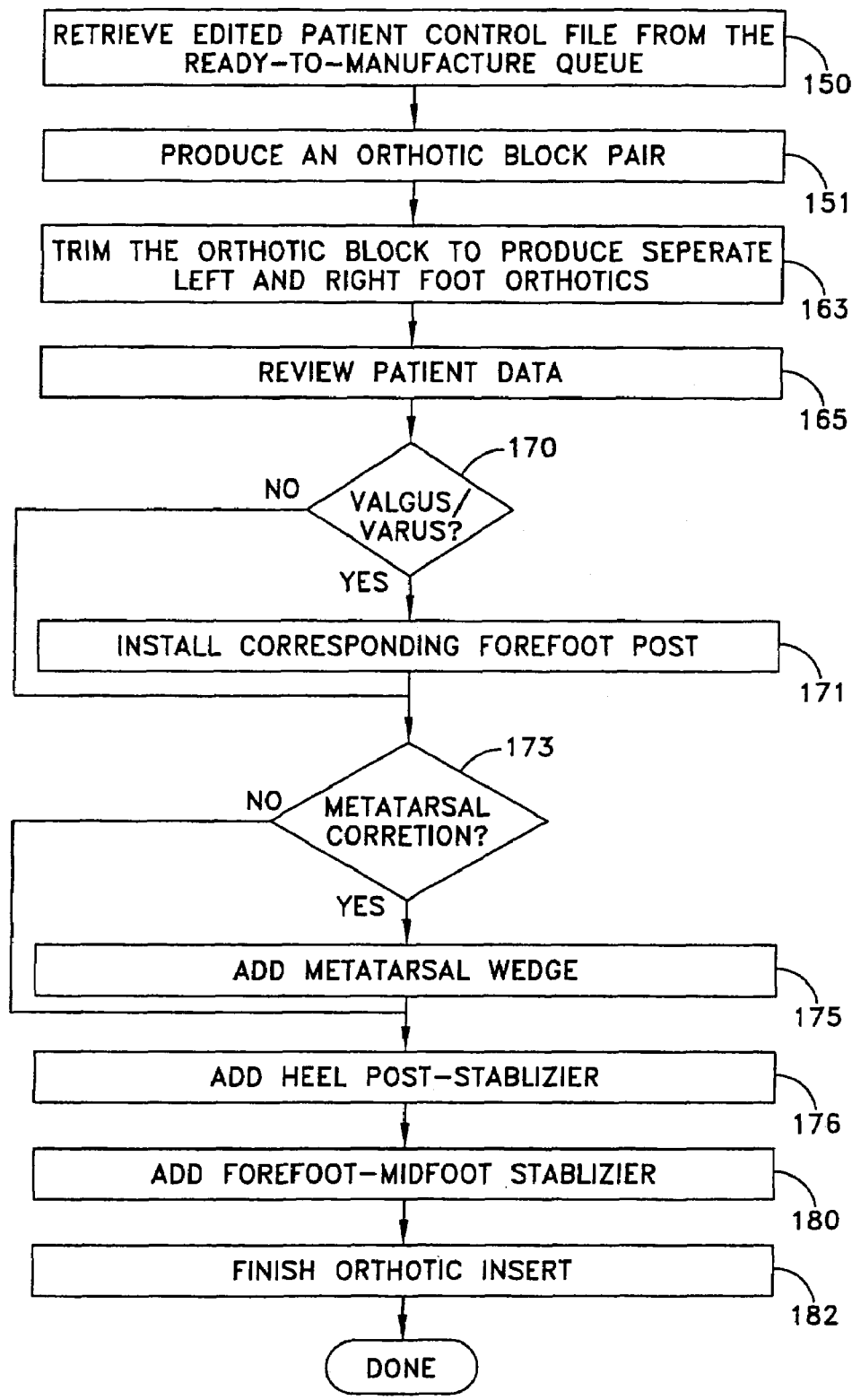
FIG. 22 is a flow diagram of the process for manufacturing an orthotic insert using the orthotics from the orthotic block shown from the scan of FIG. 21.

When the time arrives for the actual manufacture of a patient's orthotic insert laboratory personnel use step 150 in FIG. 22 to retrieve the edited patient control file from the ready-to-manufacture queue 135 at step 150. Then the information is transferred to the CNC machine where, at step 151, the CNC machine 124 produces an orthotic block pair 152, shown in FIG. 23. The orthotic block pair 152 includes portions for the left and right feet at 153 and 154, respectively. With respect to the right foot, the machined block has a depressed rounded heel portion 155 and a tapered elevated arch support 156. A slightly elevated area 157 accommodates varus in the foot.

The left foot portion 153 also includes a rounded heel portion 160 with an arch support area 161 that is somewhat less pronounced than the arch support 156 for the right foot. In the left foot, there is a slight elevation 162 along the outer edge of the left foot to accommodate valgus.

Figure 23:
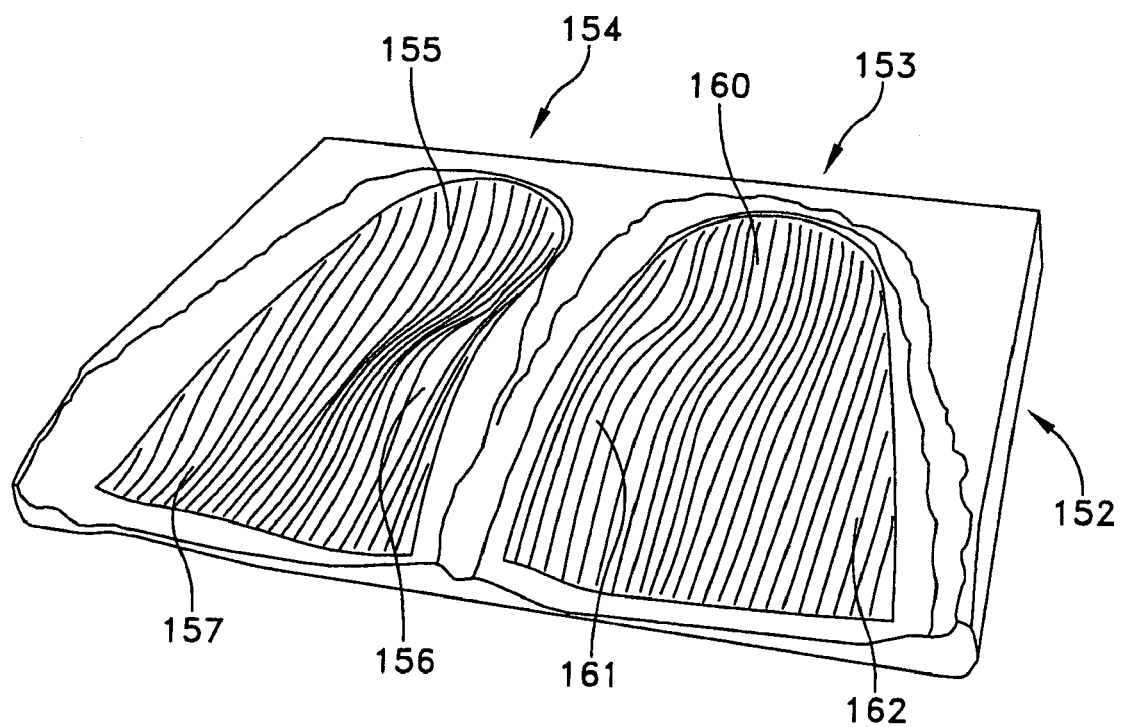
FIG. 23 is a perspective view of an orthotic block formed in accordance with this invention using the process of FIG. 22 and the scan of FIG. 21.
Figure 24:
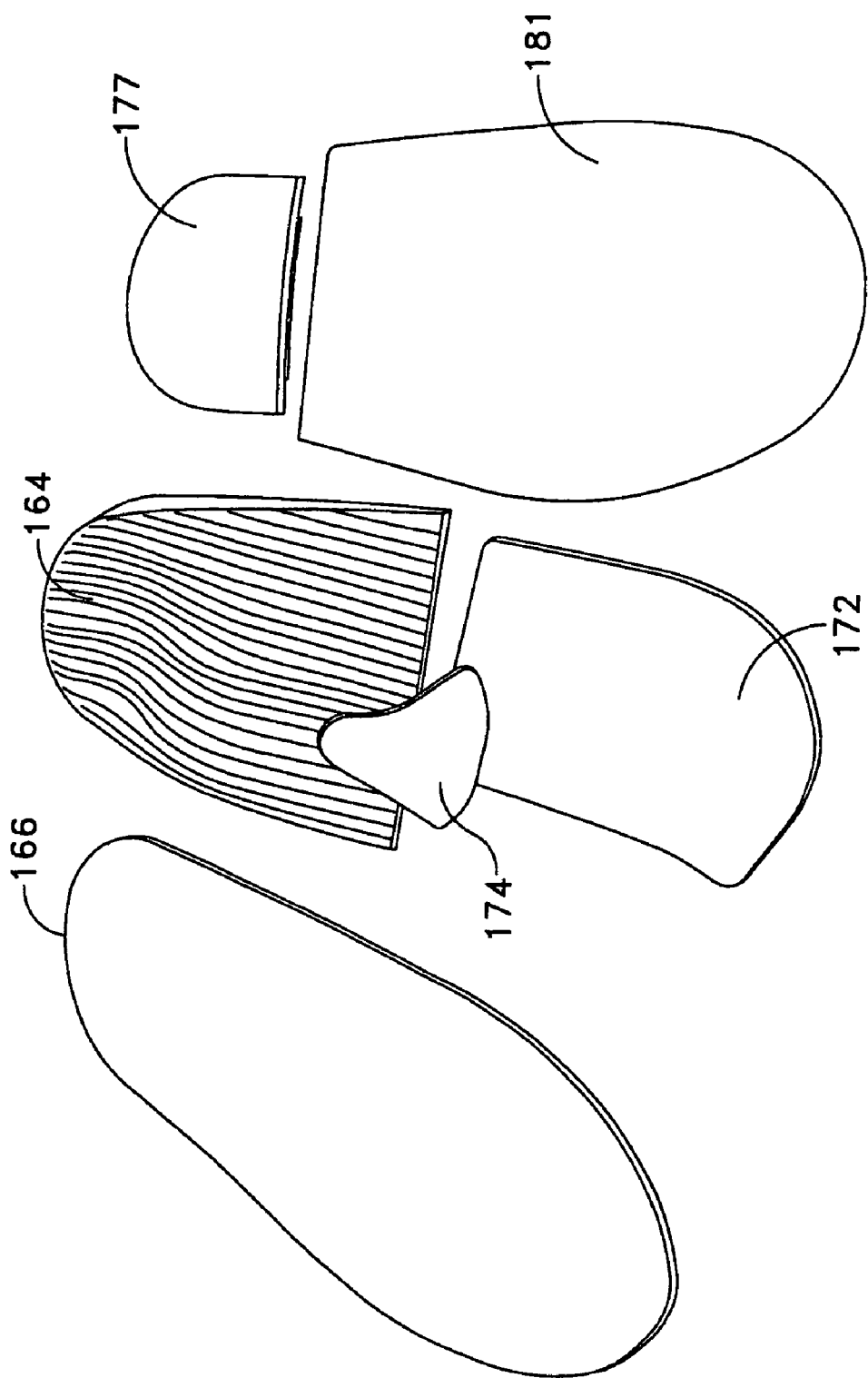
FIG. 24 is an exploded view of various components that can be used to manufacture a finished orthotic footbed.

After the production of the orthotic block pair 152 in FIG. 23, the laboratory personnel trim the orthotic block pair 152 to produce two separate orthotics with the form of an orthotic 164 shown in FIG. 24.

Referring again to FIG. 22, step 165 represents the review of the patient data, such as that shown in the patient evaluation form of FIG. 17, by laboratory personnel. The personnel obtain information from this data that are useful in a number of different ways. Information about the weight, age shoe types and activities is useful in the selection of components of specific materials for providing different characteristics. For example, FIG. 24 depicts a top cover 166. The top cover 166 may be selected to cover only the rear foot and midfoot or the entire foot depending upon the anticipated use of the orthotic insert. Thus for example as shown in FIG. 22, step 182 represents the selection and installation of a top cover on each orthotic based upon that information. That is and referring to FIG. 24, the top cover 166 is positioned on top of the orthotic 164. In this particular case, the top cover covers the full length of the person's foot, while the orthotic 164 is designed to underlie the rear foot and midfoot.

The patient data reviewed in step 165 alerts laboratory personnel to any patient anatomical deformities to be accommodated in completion of the orthotic insert. Step 170 in FIG. 22 represents a decision made by laboratory personnel as to whether a valgus or varus accommodation is needed. If it is, step 171 represents the installation of a corresponding forefoot post. FIG. 24 depicts a section of material 172 representing the material that might be used in a forefoot post. Referring to FIG. 23, the orthotic for the right foot exhibits varus because the surface tapers from the medial dynamic column to the load bearing column. In this situation, the material 172 is shaped to continue that taper forward from the orthotic insert 154 toward the forefoot. Transversely the material extends from the medial column to the $4^{th}$ metatarsal and tapers in thickness from the medial column to the $4^{th}$ metatarsal. Similarly, the orthotic 153 for the left foot has a surface 162 with a profile that is consistent with valgus. The forefoot post would then taper from the lateral load bearing column under the $5^{th}$ metatarsal to the medial dynamic column under the $2^{nd}$ metatarsal and would extend from the front of the orthotic 153 to underlie the balance of the midfoot and the forefoot.

Step 173 in FIG. 22, represents the determination by laboratory personnel of the need for a metatarsal correction. Essentially the metatarsal correction is provided by inserting a support 174 under the central portion of the foot at the metatarsals. This helps to elevate a transverse arch of the foot thereby to overcome a number of issues, such as dropped metatarsals and neuroma. If such a metatarsal correction is required, step 175 represents the addition of the metatarsal support 174 typically to the underside of the top cover 166.

After laboratory personnel make these corrections by the addition of any posts or wedges to the underside of the top cover 166, the laboratory personnel use step 176 to add a heel post-stabilizer 177 to the bottom of the orthotic 164. Step 180 represents the addition of a midfoot and forefoot stabilizer 181.

Figures 25A, 25B:
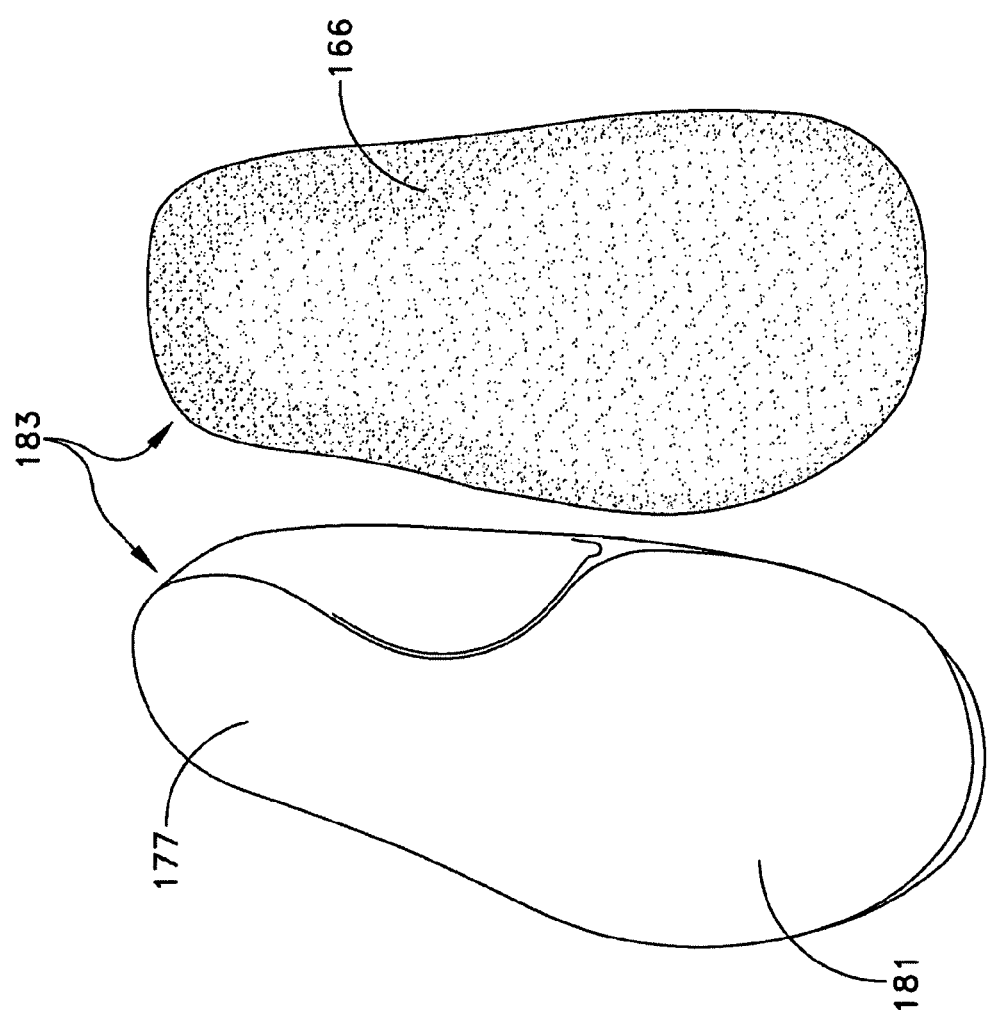
FIG. 25 discloses bottom and top perspective views of the finished orthotic footbed.

When these steps have been completed, laboratory personnel use step 182 to grind and finish the final orthotic footbed 183 as shown in FIG. 25 viewing the top of the insert 183 on the right of FIG. 25 and particularly the top cover 166 and where at the left with the orthotic inverted with the heel post-stabilizer 177 and the forefoot-midfoot stabilizer 181 visible. An orthotic footbed as shown in FIG. 25 for each foot is then packaged for return to the practitioner who made the original measurements for insertion in the patient's footwear.

As will now be apparent, an orthotic insert shown in FIG. 25, has several advantages. First, it defines a rear foot support surface that moves the individual's feet to the referenced neutral position. Further, as the scan includes the entire foot from the metatarsals past the heel, the air cushion provides a support that accommodates valgus or varus or other anatomical deformation. Combining the precision of laser scanning and CNC control machines permits the information provided by the scanning apparatus to be faithfully reproduced in the orthotic 164 of FIG. 24. Moreover, scanning the foot in a semi-weight bearing condition further minimizes the empirical inputs normally required provided by the prior art casting system. Consequently measurement apparatus provides a means for supplying information approaching the information obtained through the gold standard of plaster casts and molds without any of the disadvantages of that process.

Further, as will now be apparent, the overall process of this invention produces orthotic footbeds that are comparable in quality to those produced by the prior art cast/mold gold standard process. However, the process of this invention is significantly more efficient. Assume that a patient interview requires 10 minutes. The cast/mold process takes up to 30 minutes or more, so a practitioner must spend up to 40 minutes with a patient. The scan of FIG. 13 is the digital equivalent of a cast and replaces it. The time required to obtain scans for both feet is less than 5 minutes. As a result the time a practitioner must spend with a patient reduces from 40 minutes to 15 minutes. Moreover, the investment in the examination station required by this invention is significantly less than the investment required for the materials, equipment and office space required for making casts.

Figure 21:
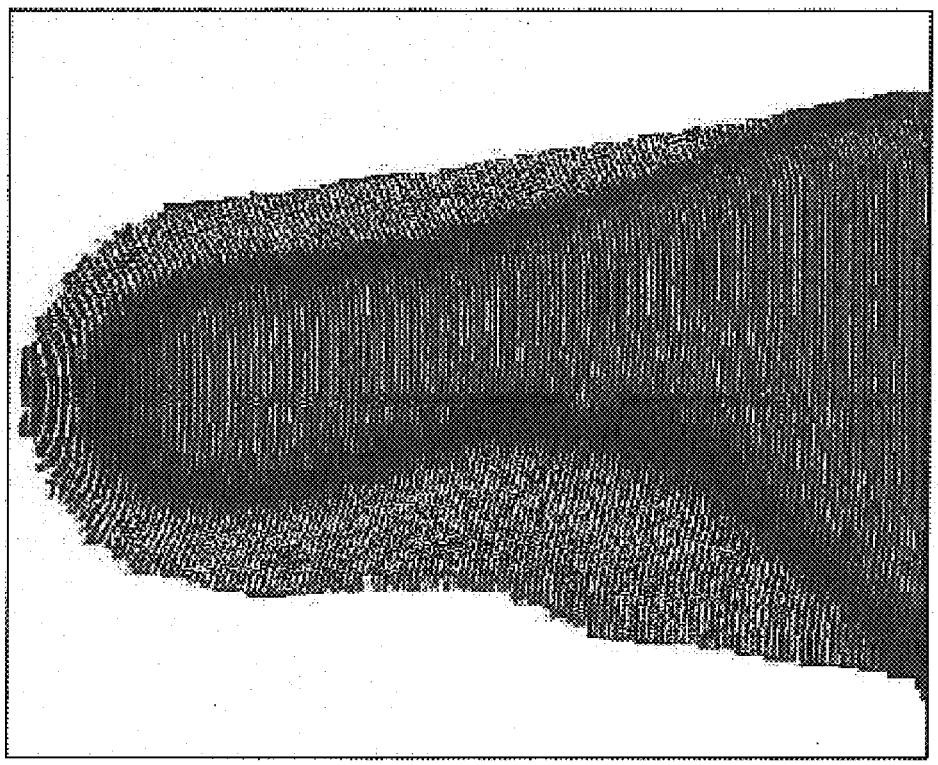
FIG. 21 depicts the scan of FIG. 13 after it is edited in accordance with the flow diagram of FIG. 20.

Similarly, a production facility will operate more efficiently with this invention than with the gold standard process. It takes only a couple of minutes to convert the image of FIG. 13 to the image of FIG. 21. The image of FIG. 21 is the digital equivalent of the mold and requires no modification. It is readily converted into an orthotic block with only minimal personnel involvement. Consequently, this invention eliminates the effort for making the mold, modifying the mold and casting the orthotic. Further it eliminates the investment in the molding equipment and the expenses involved in materials and time for making the orthotics by the molding process. Comparisons indicate that the time to prepare a finished orthotic footbed with the gold standard process is 60-90 minutes; this invention can reduce that time to about 20 minutes.

This invention has been described in terms of specific implementations of a measurement apparatus and manufacturing facilities. It will be apparent to those of ordinary skill in the art that a number of variations can be made. Measurement apparatus having form factors that differ from those shown in the figures could be substituted so long as the measurement apparatus defines a reference plane and enables a laser scan to occur. Such measurement apparatus could also be lowered to be flush with the platform 54 in FIG. 6. Different materials may be used for the flexible membrane 81. Specific dimensions have been given by way of example. Devices could also be made with other dimensions while still providing the function of the various structures in the measurement apparatus.

Therefore it is the intent of the appended claims to cover all such variations and modifications as come within the true spirit scope of this invention.

What is claimed as new and desired to be secured by Letters Patent of the United States is:

1. Apparatus at an examination station for obtaining measurements for use in the construction of an orthotic block for use in the construction of orthotic footbeds for a patient's footwear wherein each of the patient's feet is characterized by a forefoot, a midfoot and a rear foot, said apparatus comprising:

A. reference means for defining a reference plane,

B. foot capture means for capturing one of the patient's feet in a semi-weight-bearing referenced neutral position with the forefoot supported on the reference plane and the rear foot floating above the reference plane, C. array measurement means for obtaining an array of measurements representing the distances between the reference plane and an array of positions on the bottom of at least the rear foot of the patient's captured foot, and D. storage means for storing the measurements from said array measurement means for use in the construction of the orthotic block.

2. Apparatus as recited in claim 1 wherein said foot capture means includes air cushion means for elevating the heel above the reference plane during the operation of said measurement means.

3. Apparatus as recited in claim 2 wherein said air cushion means includes a flexible membrane overlying portions of said reference means.

4. Apparatus as recited in claim 3 wherein said air cushion means includes air pump means for inflating said membrane whereby said membrane moves into contact with the plantar surface to contain and to support the plantar fasciae and foot structure of the patient's foot.

5. Apparatus as recited in claim 4 wherein said air cushion means includes support means for defining said flexible membrane with a forefoot portion at the reference plane, a rear foot portion elevated above the reference plane and an intermediate sloped portion between said forefoot and rear foot portions.

6. Apparatus as recited in claim 5 wherein said storage means includes means for generating a patient file with the measurements from each of the patient's feet.

7. Apparatus as recited in claim 3 wherein said array measurement means includes scanning means for scanning the surface of the flexible membrane thereby to obtain the array of measurements.

8. Apparatus as recited in claim 7 wherein the patient's foot is placed on the top of said flexible membrane and wherein said reference means includes a transparent plate on the opposite side of said flexible membrane positioned whereby at least the patient's rear foot is coextensive therewith and means for supporting said transparent plate, said scanning means including three-dimensional laser scanning means for directing a scanned laser beam through said transparent plate onto the opposite side of said flexible membrane.

9. Apparatus as recited in claim 8 wherein said transparent plate lies under the patient's midfoot and rear foot and said supporting means is opaque and includes a portion for receiving the patient's forefoot.

10. Apparatus as recited in claim 9 wherein said flexible membrane includes a reference line at the interface between said flexible membrane and said portion of said supporting means for receiving the patient's forefoot.

11. Apparatus as recited in claim 10 wherein said storage means includes means for generating a patient file with the measurements from each of the patient's feet obtained from said laser scanning means.

12. Apparatus as recited in claim 11 wherein said storage means includes a digital computer system programmed for controlling the operation of said laser scanning means and the transfer of measurements from said laser scanning means to said storage means.

13. Apparatus as recited in claim 1 where said storage means includes means for generating a patient file with the measurements from each of the patient's feet.

14. Apparatus as recited in claim 13 additionally adapted for connection to an orthotic production facility including:
   i) automated machining means for machining an orthotic block based upon input data, and
   ii) means for converting the data in the patient file the input data used by said machining means whereby said machining means produces an orthotic block.

15. Apparatus as recited in claim 14 wherein the data in the patient file includes relevant and irrelevant information and said converting means includes:

a) editing means for deleting the irrelevant data from said patient files to produce an edited patient file, and
   b) means for converting the data of the edited patient file into data for controlling said automated machining means.

16. Apparatus as recited in claim 14 wherein said production facility is located remotely from said examination station and including means for establishing a communications path between said examination station and said production facility.

17. A method for obtaining measurements for use in the construction of an orthotic footbed for a patient's footwear wherein a patient's foot is characterized by a forefoot, a midfoot and a rear foot, said method comprising:
   A. defining a reference plane,
   B. capturing the patient's foot in a semi-weight-bearing referenced neutral position with the forefoot supported on the reference plane and the rear foot floating with the heel elevated above the reference plane,
   C. obtaining an array of measurements representing the distances between the reference plane and an array of positions on the bottom of at least the patient's captured rear foot, and
   D. converting the array of measurements to an orthotic footbed.

18. A method as recited in claim 17 wherein said foot capture includes pneumatically elevating the heel above the reference plane.

19. A method as recited in claim 18 wherein said pneumatic elevation includes forming an air cushion with a flexible membrane overlying portions of the reference.

20. A method as recited in claim 19 wherein said capture includes moving the patient's rear foot to a referenced neutral position while said air cushion is deflated and then inflating the air cushion to lock the forefoot and midfoot against the rear foot.

21. A method as recited in claim 20 including forming an upper surface of the air cushion with a forefoot portion at the reference plane, a rear foot portion elevated above the reference plane and an intermediate sloped portion between said forefoot and rear foot portions.

22. A method as recited in claim 21 wherein said conversion includes generating a patient file with the measurements from each of the patient's feet.

23. A method as recited in claim 19 wherein said array measurement includes scanning the surface of the flexible membrane thereby to obtain the array of measurements.

24. A method as recited in claim 23 wherein the patient's foot is placed on the top of the flexible membrane and wherein the reference means includes a transparent plate on the opposite side of the flexible membrane positioned whereby at least the patient's rear foot is coextensive with a portion of the flexible membrane and means for supporting said transparent plate, said scanning including directing a scanned laser beam through said transparent plate onto the opposite side of said flexible membrane thereby to obtain a three-dimensional scan of at least a portion of the bottom of the flexible membrane containing the patient's foot.

25. A method as recited in claim 24 wherein said scanning is of the patient's midfoot, rear foot and a portion of the forefoot.

26. A method as recited in claim 17 wherein said conversion includes:
   i) machining an orthotic block based upon data in the patient file, and
   ii) converting the orthotic block into at least one orthotic footbed.

27. A method as recited in claim 26 wherein the data in the patient file includes relevant and irrelevant information and said conversion includes:
   a) deleting the irrelevant data from said patient files to produce an edited patient file, and
   b) converting the data from edited patient file into data for controlling said machining.

28. A method as recited in claim 27 wherein the orthotic block has a machined portion for each of the patient's feet including the steps of:
   i) separating the machined orthotic block into an orthotic for each of the patient's feet;
   ii) applying a top cover to the top of each of said orthotics, and
   iii) applying a stabilizer to the bottom of each of said orthotics thereby to produce an orthotic footbed for each of the patient's feet.

29. A method as recited in claim 28 wherein said stabilizing application includes the steps of applying a heel stabilizer to the rear foot-portion and a forefoot-midfoot stabilizer to be under the patient's forefoot and midfoot.

30. A method as recited in claim 28 wherein a patient has an anatomical deformity, said method including applying a corrective element intermediate the top cover and the forefoot-midfoot stabilizer.

* * * * *